US012782277B2

(12) United States Patent
Chu et al.

(10) Patent No.: US 12,782,277 B2
(45) Date of Patent: Nov. 3, 2026

(54) PHOTONIC CHIP FOR MONITORING ACTIVITIES OF LIVING CELLS

(71) Applicant: THE UNIVERSITY OF HONG KONG, Hong Kong (HK)

(72) Inventors: Zhiqin Chu, Hong Kong (HK); Yuan Lin, Hong Kong (HK); Jixiang Jing, Hong Kong (HK); Yong Hou, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 589 days.

(21) Appl. No.: 17/846,056

(22) Filed: Jun. 22, 2022

(65) Prior Publication Data

US 2023/0003644 A1 Jan. 5, 2023

Related U.S. Application Data

(60) Provisional application No. 63/217,773, filed on Jul. 2, 2021.

(51) Int. Cl.
*G01N 21/41* (2006.01)
*G01N 21/43* (2006.01)
*G01N 33/483* (2006.01)

(52) U.S. Cl.
CPC ......... *G01N 21/4133* (2013.01); *G01N 21/43* (2013.01); *G01N 33/4833* (2013.01); *G01N 2021/414* (2013.01)

(58) Field of Classification Search
CPC ............... G01N 21/4133; G01N 21/43; G01N 33/4833; G01N 2021/414; G01N 2021/7776; G01N 21/552; G01N 21/7703
See application file for complete search history.

(56) References Cited

U.S. PATENT DOCUMENTS

| | | | | |
|---|---|---|---|---|
| 4,964,707 | A * | 10/1990 | Hayashi | G02B 21/14 359/371 |
| 6,288,527 | B1 | 9/2001 | Sugihara et al. | |
| 7,192,752 | B2 | 3/2007 | Xu et al. | |
| 7,470,550 | B2 | 12/2008 | Yoshizato et al. | |
| 10,551,313 | B1 | 2/2020 | Li et al. | |
| 2005/0014130 | A1 | 1/2005 | Liu et al. | |
| 2010/0195873 | A1 * | 8/2010 | Cui | G02B 21/367 382/106 |
| 2011/0188043 | A1 | 8/2011 | Davidov et al. | |
| 2022/0204903 | A1 * | 6/2022 | Nordon | C12M 29/20 |
| 2023/0062698 | A1 * | 3/2023 | Engel | G06T 7/557 |

OTHER PUBLICATIONS

Oh C, Isikman SO, Khademhosseinieh B, Ozcan A. On-chip differential interference contrast microscopy using lensless digital holography. Opt Express. Mar. 1, 2010;18(5):4717-26. doi: 10.1364/OE.18.004717. PMID: 20389485; PMCID: PMC2859902. (Year: 2010).*

* cited by examiner

*Primary Examiner* — Hwa Andrew Lee
(74) *Attorney, Agent, or Firm* — Amin, Turocy & Watson, LLP

(57) ABSTRACT

Disclosed are systems and methods of label-free detecting cellular physiological activities involving monitoring local refractive index changes associated with cellular physiological activities using a single ultracompact light emitting diode (LED) chip serving as a refractometer.

5 Claims, 16 Drawing Sheets

| | Sensitivity | Vertical sensing range | Size | Incubator compatibility | Integrability and miniaturization | Complexity |
|---|---|---|---|---|---|---|
| Impedance sensor | $10^{4}$–$10^{-4}$ μmol/L[5] | 0 | Small | Yes | Yes | Low (electrode pattern +readout circuit) |
| Resonant waveguide grating biosensor (RWG) | $10^{2}$–$10^{4}$ degree/RIU[6] | ~100 nm | N/A | No | No | High (Laser +spectrometer+ prism) |
| Surface plasmon resonance (SPR) | $0.4\times10^{2}$-$10^{3}$ degree/RIU[6] | ~100 nm | N/A | No | No | High (Laser +spectrometer+ prism) |
| Monolithic GaN chip | 149216 nA/ RIU* | ~500 nm* | ~ mm | Yes | Yes | Low (GaN chip+ ammeter) |

Fig. 19

PHOTONIC CHIP FOR MONITORING ACTIVITIES OF LIVING CELLS

CROSS-REFERENCE TO RELATED APPLICATIONS

This application claims priority to U.S. Provisional Application Ser. No. 63/217,773 filed on Jul. 2, 2021, the entire contents of which are incorporated herein by reference.

TECHNICAL FIELD

Disclosed are miniaturized photonic chip for label-free monitoring physiological activities of living cells.

BACKGROUND

There is a lack of cost-effective way allowing label-free and real-time optical readout of cell activities because the commonly used techniques for real-time optical readout of cell activities, such as surface plasmon resonance (SPR) and resonant waveguide grating biosensor (RWG). Both technologies have high requirements about the intensity and incident angle of laser source and the sensitivity of photo detector. Additionally, these sensor chips used are made of precious metals (e.g., gold for SPR) or integrated with specific micro/nano structures (e.g., diffraction grating for SPR) which increase the difficulties of manufacture and their associated costs. Moreover, the whole systems are difficult to miniaturize, hindering their applications accordingly.

The commonly used optical biosensors for living cell detection employ surface plasmon resonance and resonant waveguide. Both technologies exploit evanescent waves to characterize the dynamic behaviors of a biological layer at or near the sensor surface. However, these optical sensors highly rely on laser system which are costly and may lead to potential optical cytotoxicity for living cells.

Another commonly used biosensing technique relies on detecting electrical signals (e.g., impedance) to monitor change in cell status (number, morphology, adherence); however, this method might be disturbed by external electromagnetic wave because it commonly works at a fixed frequency to calculate the impedance.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

Disclosed herein are systems and methods of label-free detecting cellular physiological activities involving monitoring local refractive index changes associated with cellular physiological activities using a single ultracompact light emitting diode (LED) chip serving as a refractometer.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

BRIEF SUMMARY OF THE DRAWINGS

FIG. 19 depicts a Table of the summary of the technologies in the application of label-free living cell activities sensing; *the data was collected from this work, the vertical sensing range was calculated by the COMSOL Multiphysics software, herein, the range represent the vertical separated distance between the chip and sample layer when the intermediate is water, referred to FIG. 14.

DETAILED DESCRIPTION

Figure 1:
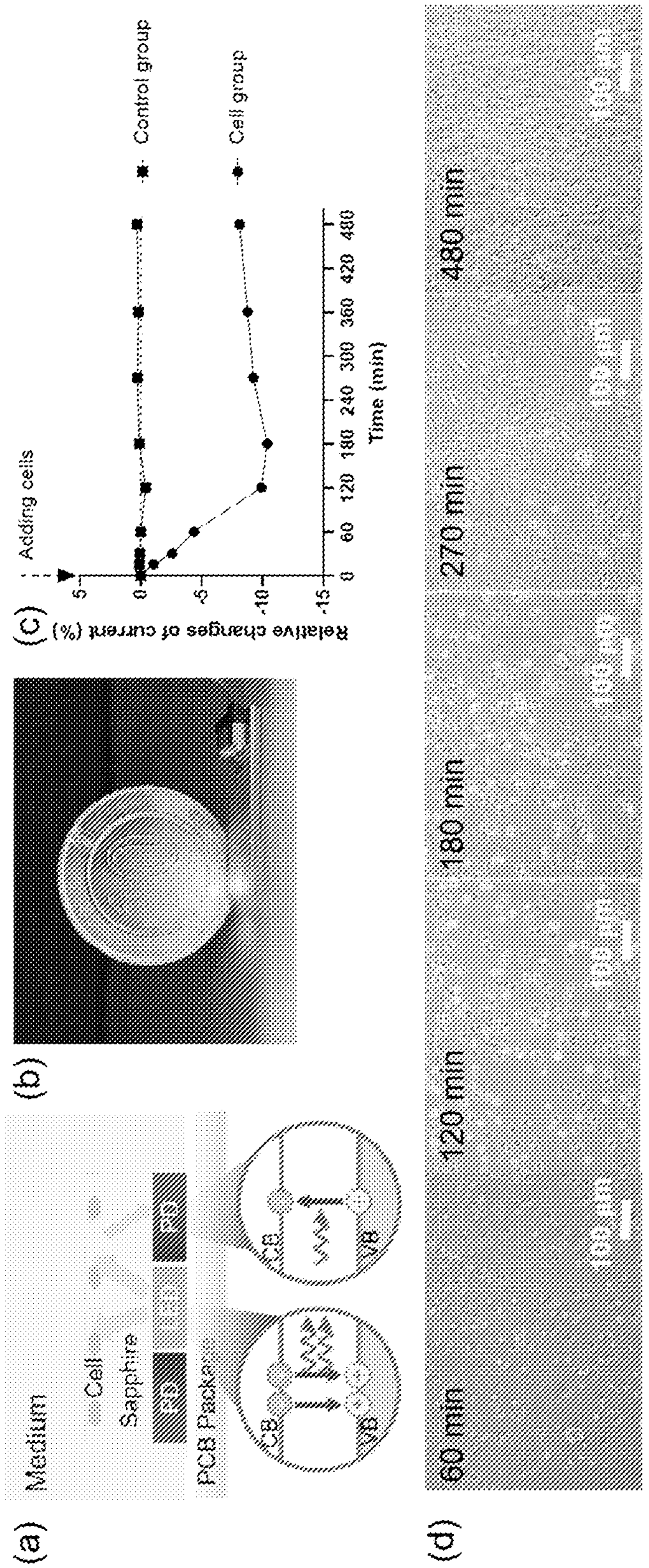
FIG. 1 depicts: (a) schematic diagram of the device working principle; (b) image of the integrated photonic chip took by mobile phone; (c) response of the sensor while real-time monitoring cell adhesion and spreading; and (d) corresponding microscope images of cells on the sapphire substrate.

Living cell label-free sensing technologies, capable of label free, high through-put and online monitoring of cell activities, such as cell adhesions, proliferation and differentiation and toxicity, play important roles in cell biology and drugs screening. So far, many techniques have been developed to fulfill the requirement of real-time and high-throughput cellular analysis, such as surface plasmon resonance (SPR), resonant waveguide grating biosensor (RWG), electric cell-substrate impedance method (ECSI) etc. Although these technologies can be employed for cellular adhesion analysis, their complicated preparation process, equipment dependence and high costs may restrict their wide applications. As described herein, the label-free detection of cellular physiological activities using a low-cost miniaturized photonic chip is demonstrated. Specifically, the local refractive index changes are monitored, as well as the morphological changes, associated with cellular activities, by using a single ultracompact LED chip serving as a refractometer. This powerful tool enables the capture, distinguish, and quantify the cell behaviors such as cell precipitation, spreading, proliferation and other cellular behaviors in a real-time manner. Furthermore, the current method can also be pushed to work at single cellular level using proper photonic structure design.

Through the compact design of a LED chip being capable of detecting refractive index changes, even the minute changes of cellular physiological activities, accompanied with refractive index changes, can be captured by monitoring the corresponding photocurrent variations of LED chip. This powerful tool enables the capture, distinguish and quantify the cell behaviors such as cell precipitation, spreading, proliferation and other cellular behaviors in a real-time manner.

The single ultracompact LED chip can be a chip-scale refractometer made of a monolithic integration of light-emitting diodes (LEDs) and photodetectors (PDs). In the single ultracompact LED chip, the amount of light reflected into PD region is determined by two parts: i) total reflection at the interface of the chip's substrate (such as for example sapphire) and the external medium; and ii) the light scattered by the substance in the external environment. Once cells adhere to the single ultracompact LED chip, the local RI (refractive index) changes induced by cells morphological dynamics (cells activity leads to different morphology) are recorded by the single ultracompact LED chip.

The dimensions of currently used chip (spatial resolution) are on the order of the ~mm or sub ~mm scale. Such can be improved using micro-/nano-LED, in order to integrate and optimize sensing chips on the microscopic scale.

As mentioned above, surface plasmon resonance (SPR), resonant waveguide grating (RWG), and resonant mirrors have been developed in the application of label free detection of cells. In this work, however, LED and PD are integrated into a microscale chip, and it is the first time for the integrated LED chip to be applied in the detection of cellular activities. Compared with these known techniques, single ultracompact LED chip exhibits lower costs, easier integration and lower power consumption, showing great potential in practical applications.

Referring to FIG. 1, in (a), a schematic diagram of the device working principle is described, showing the interaction amongst a LED, a cell and a photodetector. In (b), an image of the integrated photonic chip took by mobile phone demonstrates the relatively small size as compared to a $10 coin (Hong Kong). The Hong Kong $10 coin has a size of 24 mm diameter, 3 mm thickness, and 15.6 mm diameter of center plug. In (c), a graph plots time (x-axis) versus change of current (y-axis) to demonstrate the response of the sensor while real-time monitoring cell adhesion and spreading. In (d), five microscope images of cells morphology are shown over time (at 60 min, 120 min, 180 min, 270 min, and 480 min) on a sapphire substrate. (c) and (d) are further discussed in the experimental section below.

Figure 2:
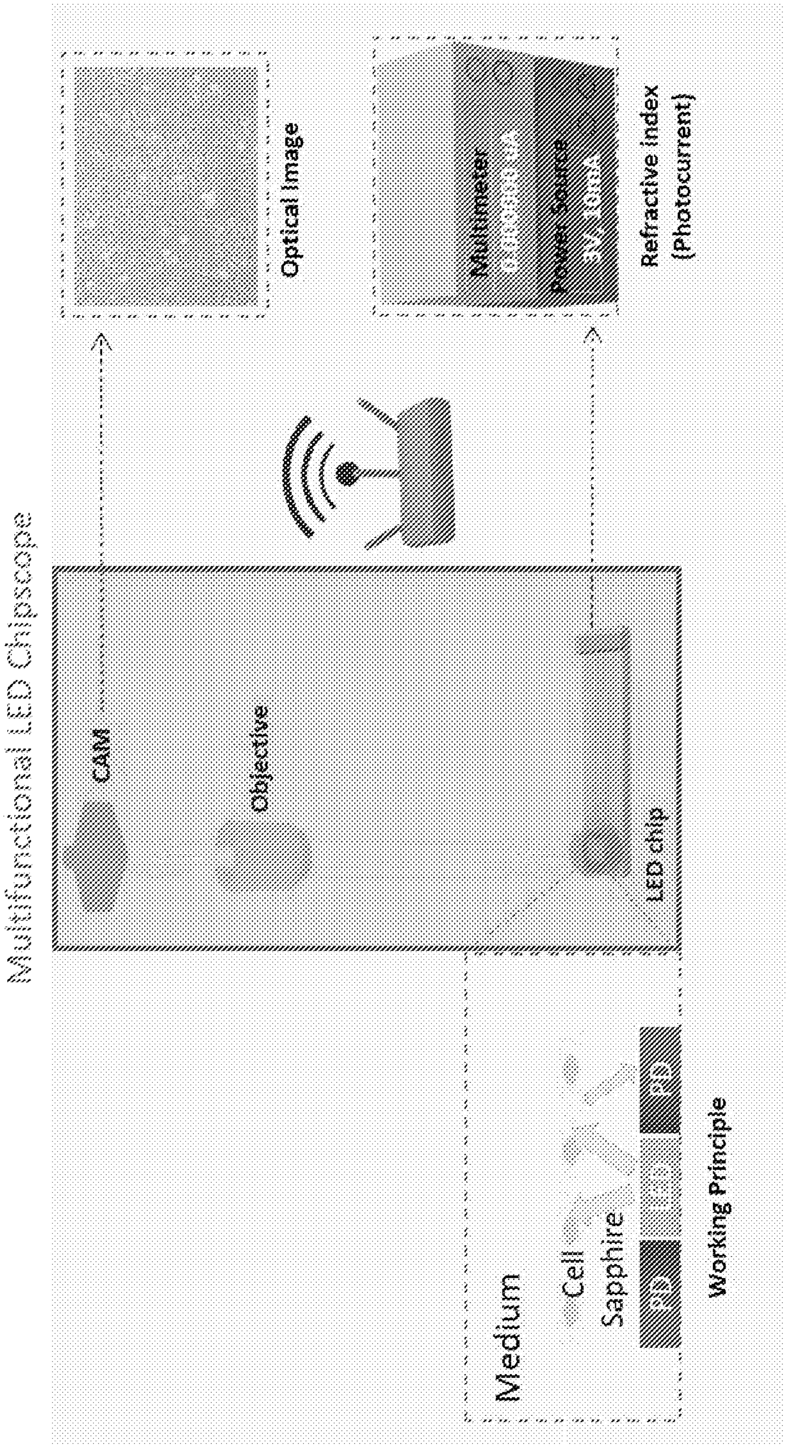
FIG. 2 depicts schematics of a multifunctional LED Chip-scope.

Referring to FIG. 2, the schematics of a multifunctional LED Chipscope are illustrated. Notice the current power supply and data transmission (wire) can be easily upgraded to a battery and wireless version. This facilitates the miniaturized sensing device being even more practical for usage, like inside a living cell incubator for long term study.

Applications of Sensing Device for Label-Free Monitoring Physiological Activities As described herein, a label-free living cell behavior detection platform is established by a cost-effective miniaturized LED photonic chip. The chip enables us to online monitor the dynamics of local RI at the interface between chip surface and the medium.

As is known that cell adhesion under both in vitro and in vivo conditions progresses through passive adsorption to the surface, attachment, spreading and the formation of focal adhesions, and it is further modulated by signalization processes, extracellular matrix components, mechanical or chemical stimulus. Therefore, the dynamic cell adhesion can directly reflect the cell states and activities. These dynamic cell adhesions lead to a significant change of RI in cells, which can be potentially utilized to develop a living cell activity sensor by measuring the change of the refractive index caused by the cell adhesions.

Monitoring the Cells Treated with Inhibitors

Figure 3:
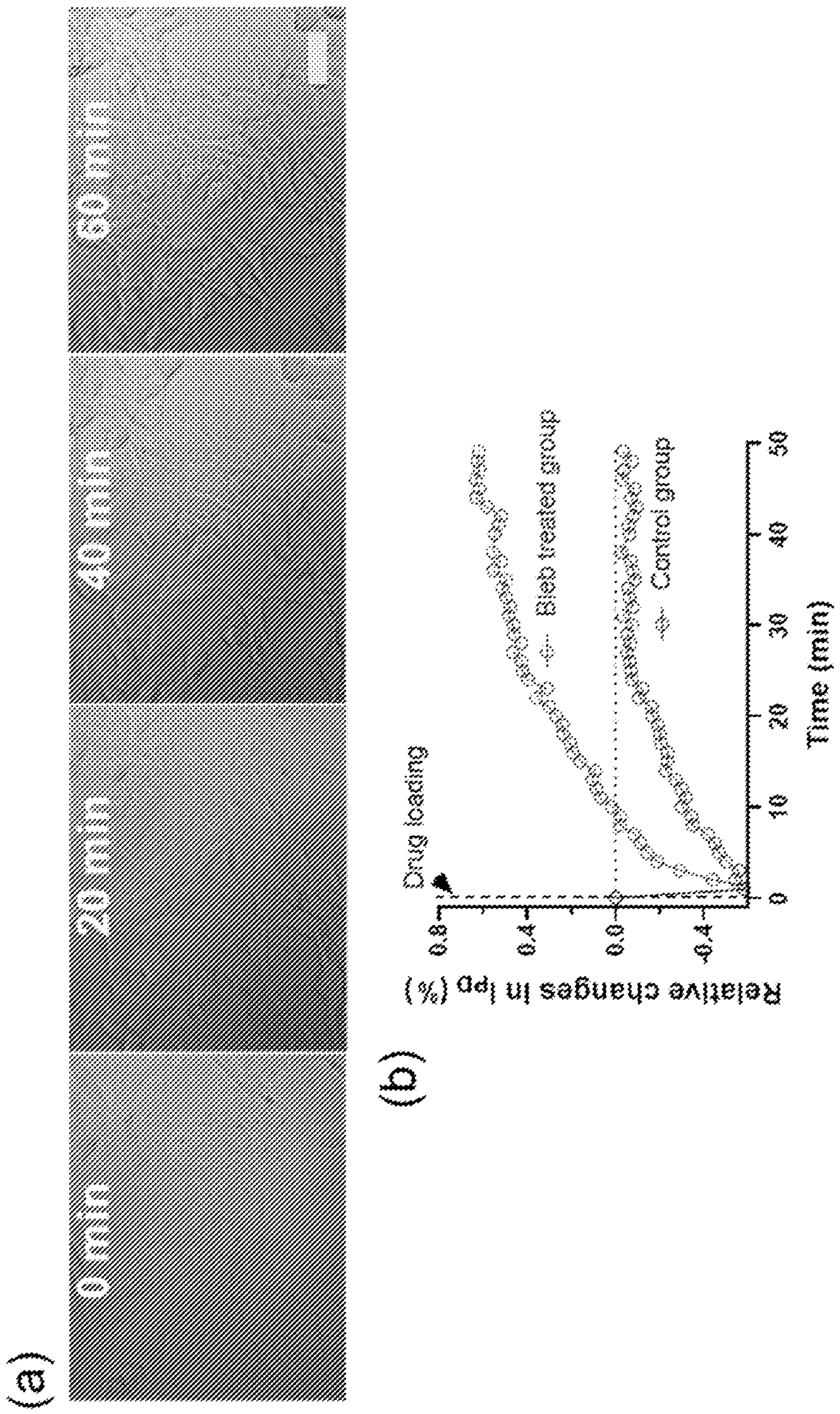
FIG. 3 depicts label-free monitoring of cell dynamics after treated with blebbistatin: (a) representative images of 3T3 cells treated with blebbistatin (50 μM) at different time points, scale bar indicates 50 μm; and (b) the relative of optical current as a function of time during the inhibitor treatment.

Referring to FIG. 3, label-free measurements of the NIH 3T3 cell adhesion treated with/without a myosin inhibitor blebbistatin (50 μM, 50 min) is shown. Normalized relative changes of current for cells treated and untreated group as a function of time. Optical images of 3T3 cells before and after the inhibitor treatment are shown. Blebbistatin is used to induce the cell morphology changes by inhibiting the myosin II activity. Myosin II is a critical determinant of contractile characteristics of cell motility and cell adhesion in several tissue types. After treatment with the drugs (50 μM), the cells gradually shrank in the next 1 h, showing increased cell gaps and dendritic cell morphologies (FIG. 3*a*). As expected, an increase in photocurrent is observed during this period due to the decrease of the cell coverage area on the chip surface (FIG. 3*b*).

In the first example, a cell contractility inhibitor, blebbistatin, was utilized to suppress the activity of cell motor protein myosin. This inhibitor can decrease the tension of actin stress fibers and minimize the focal contacts between cells and substrate. After treated for 50 min, the cells showed a shrinked morphology, and the relative optical current exhibited an increase of 1.02% compared to the control group.

Monitoring the Cells Treated with Anti-Cancer Drugs

Figure 4:
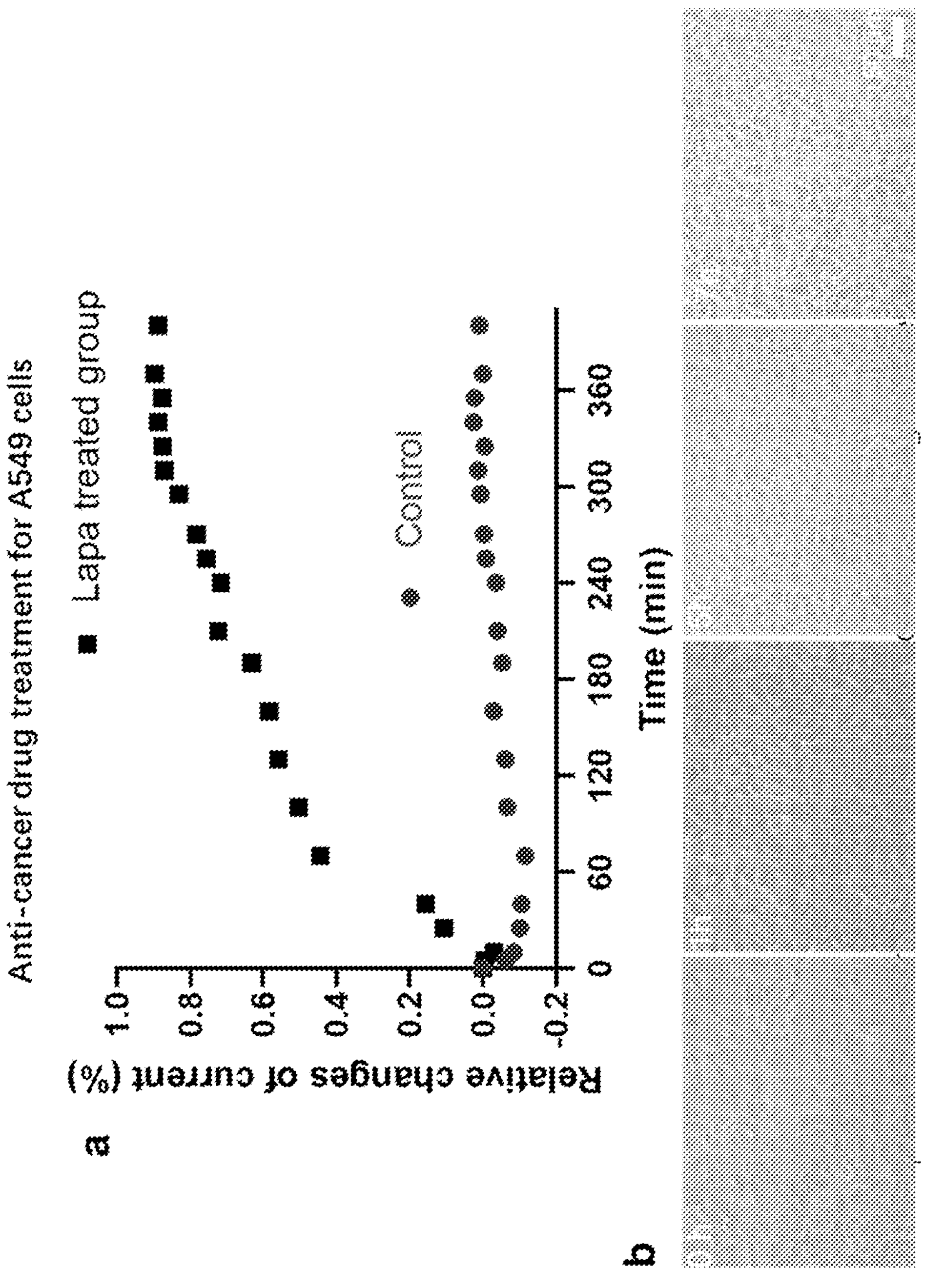
FIG. 4 depicts label-free measurements of the A549 cell adhesion treated with/without an anticancer drug β-Lapachone.

Referring to FIG. 4, label-free measurements of the A549 cell adhesion treated with/without an anticancer drug β-Lapachone (20 μM) for 7 hours are shown. In a), the structure of the β-Lapachone is shown. In b), microscopic images of normalized relative changes of current for cells treated and untreated group as a function of time. In c), optical images of A549 cells after the inhibitor treatment at different time points.

In the second example, an anticancer drug, β-Lapachone, was utilized to induce the apoptosis of A549 cells. During the 5 hours of drug treatment, the morphologies of cells changed overtime, which correspond to the gradually increased photocurrent response monitored by the LED sensor. (FIG. 4*a* and 4*b*).

Overall, these results indicated the sensing platform is capable of label-free detection of dynamic initial cell adhesion and the cell adhesion changes induced by drug treatment, which shows great potential in the applications of drug screening and adhesion based living cell sensing.

The ability to quantitatively monitor various cellular activities is critical for understanding their biological functions and the therapeutic response of cells to drugs. Unfortunately, existing approaches such as fluorescent staining and impedance-based methods are often hindered by their multiple time-consuming preparation steps, sophisticated labeling procedures, and complicated apparatus. The cost-effective, monolithic GaN photonic chip is demonstrated herein as an ultrasensitive and ultracompact optical refractometer. Here, for the first time, the so-called GaN chipscope to quantitatively monitor the progression of different intracellular processes in a label-free manner. Specifically, the GaN-based monolithic chip enables not only a photoelectric readout of cellular/subcellular refractive index changes but also the direct imaging of cellular/subcellular ultrastructural features using a customized differential interference contrast (DIC) microscope. The miniaturized chipscope adopts an ultra-compact design, which can be readily mounted with conventional cell culture dishes and placed inside standard cell incubators for real-time observation of cell activities. As a proof-of-concept demonstration, the following applications are explored: 1) cell adhesion dynamics monitoring, 2) drug screening, and 3) cell differentiation studies, highlighting its potential in broad fundamental cell biology studies as well as in clinical applications.

Moving beyond the mere "snapshot" provided by conventional endpoint assays (e.g., colorimetry), live cell sensing technologies have become more popular recently in biosensor development due to their ability to achieve real-time monitoring of biological processes such as adhesion, proliferation, and apoptosis. This ability may eventually lead to important new applications in drug discovery, cell invasion and migration monitoring, and toxicity detection. In particular, the rapidly advancing biotechnology industry has called for sensors with features such as miniaturization, intellectualization, expansibility, multi-functionalization and low cost.

Herein, described is the development of a low-cost, highly integrated, and incubator-compatible GaN-based RI chipscope for label-free monitoring of cellular activities. Specifically, the chip incorporating a mini-DIC microscope allows not only to perform real-time photocurrent measurement (and hence track changes in cell morphology, motions and cell-cell interactions), but also to collect brightfield live-cell images simultaneously. Utilizing this chipscope, the adhesion-spreading-detaching dynamics of cells is successfully tracked. The device is also capable of capturing drug-induced cancer cell apoptosis and immune cell differentiation, demonstrating its potential for use in practical biosensing applications.

Design of GaN Chipscope for Sensing and Imaging

Figure 5:
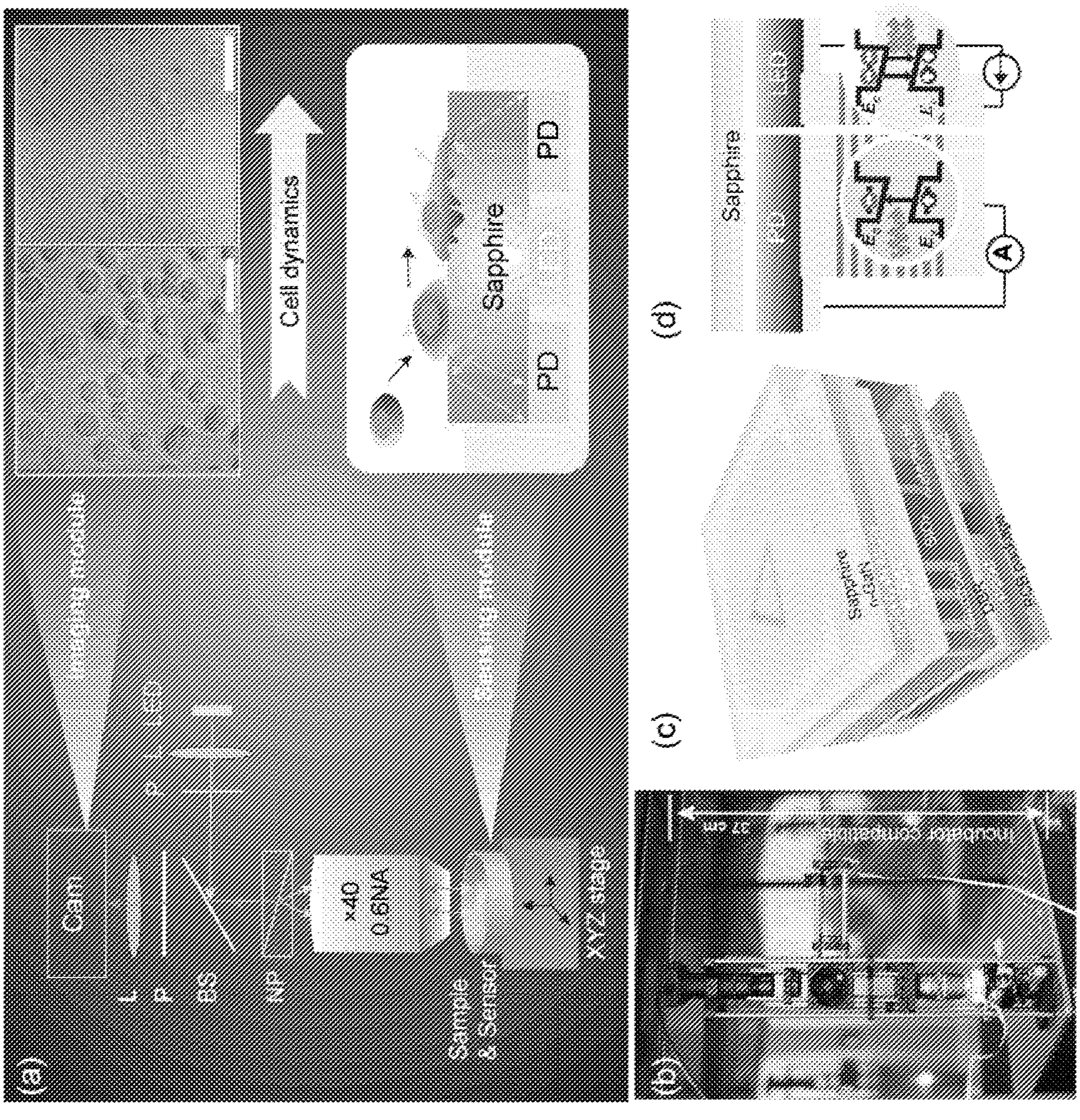
FIG. 5 depicts another working principle of the GaN chipscope: (a) the optical setup of the monolithic GaN photonic chipscope. Cam: camera, L: lens, P: polarizer, BS: beam splitter, NP: Normarski prism, the insert (upper) shows the optical image of the cells obtained from the mini-DIC scope, the insert (bottom) indicates the mechanism of sensing: the chip works as a refractometer for measuring living cell activities associated with RI changes, and scale bar indicates 50 μm; (b) optical images of the GaN chipscope inside the cell incubator; (c) schematic composition of the adopted InGaN-based monolithic photonic chip; and (d) schematic diagram depicting the different mechanisms of emission and detection using the same quantum structure.
Figure 11:
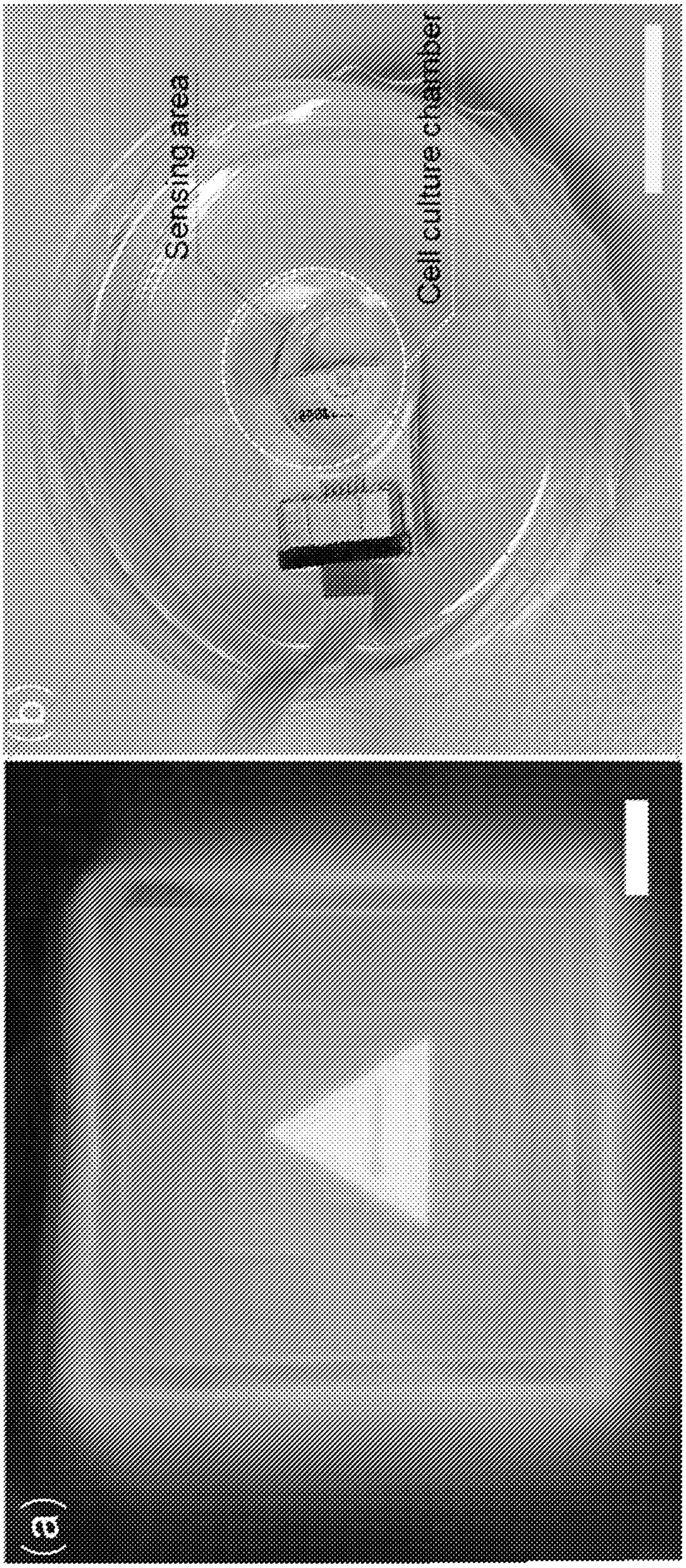
FIG. 11 depicts images of the GaN chip and the cell chamber integrated with the chip: (a) the image of the GaN chip that was lightened up, scale bar indicates 200 μm; and (b) the image of the cell chamber on the GaN chip, scale bar indicates 1 cm.

Real-time monitoring of the activities of living cells and their therapeutic responses is vital for applications such as disease diagnosis and pharmacodynamic analysis. Here, an integrated miniature sensing and imaging system is employed to achieve this. Specifically, the system consists of two core components: i) a monolithic optoelectronic chip; and ii) a mini-differential interference contrast (DIC) microscopy unit (FIGS. 5 *a* and *b*). The former integrated light-emitting diode (LED) and photodetector (PD) on a GaN/sapphire chip through wafer-scale processes (See Methods). Importantly, the LED and PD parts were electrically isolated to each other, but can work independently by connecting to a current source and an ammeter, respectively, as shown in FIG. 5*d*. In this sense, a triangular LED with a side length of 238 μm was located at the center of the chip, whereas the surroundings corresponded to the light-detecting region, as shown in FIG. 5*c* and FIG. 11*a*. The DIC unit used a prism to split the linearly polarized light into two rays which experienced different optical paths due to the varied thickness of the specimen. Hence, the light beams with different phases caused by optical path differences underwent interference and generate amplitude fluctuations to form the DIC images (FIG. 5*a*). The exposed sapphire substrate is favorable in direct contact with cells, as shown in FIG. 5*a*. Several such miniature systems were fabricated on a 1×1 $mm^2$ chip, bonded on a printed circuit board (PCB), to connect with a current source and ammeter easily. Additionally, to ensure that cells could be cultured on the chip, a mini-polydimethylsiloxane (PDMS) chamber (1×1 $cm^2$) is fabricated to enclose the chip (FIG. 11). Importantly, the dimensions of the device were only 7×17×37 cm, allowing it to be placed and work in a cell incubator (FIG. 5*b*). Detailed setup descriptions are provided in Methods below.

Sensing Principle of the Optoelectronic Chip

As a monolithic integration design of the chip, the same shared sapphire substrate can realize the light coupling from the LED to the PD without any external optics, as shown in FIG. 5*a*. In particular, when the lights emitted from LED reached external media with a low RI (i.e., $n_{media}<n_{sapphire}$), total internal reflection occurred at the sapphire/media interface, causing some light to be reflected into the light-detecting region. The intensity of the reflected light is then detected by the PD. Since the critical angle enlarges as the refractive index increases, less light is reflected back to the PD, resulting in a decrease in the photocurrent. When the cells are in contact with the chip surface, the sensor provides a rapid photocurrent response due to the obvious RI change from sapphire-culture medium (1.78 to 1.337) to sapphire-cells (1.78 to 1.343-1.48). Furthermore, the formation of strong cell-substrate adhesion and/or the evolution of cell morphology could also result in changes in the recorded photocurrent.

Demonstration of Optical and Electrical Performance and Sensing Ability

Figure 6:
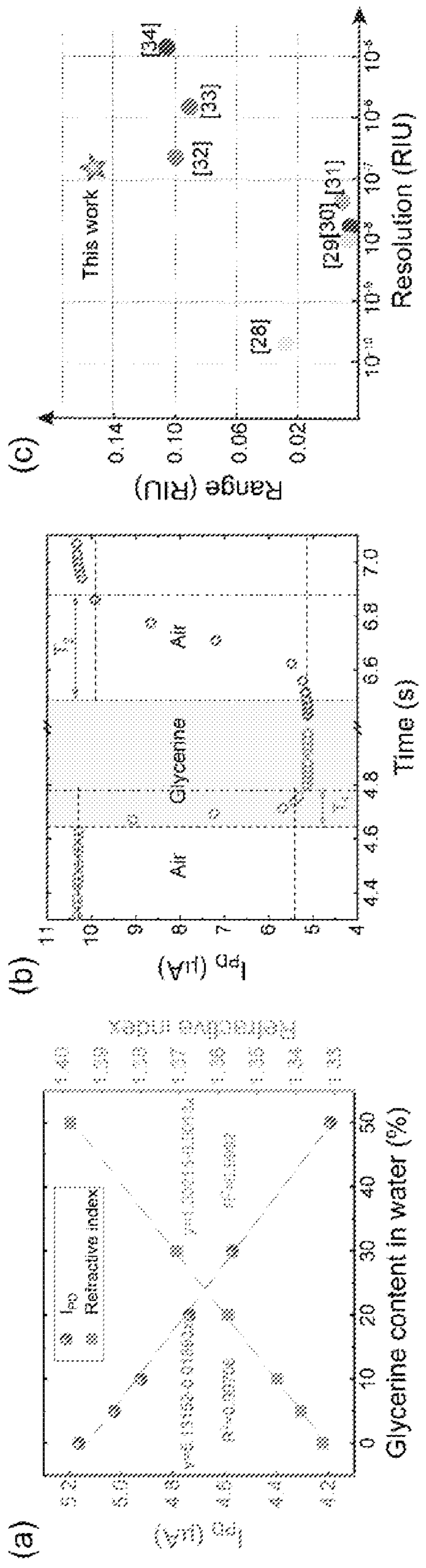
FIG. 6 depicts validating the sensing capability of the GaN chip in the model system: (a) plot of the measured refractive index using the Abbe refractometer (orange square) and photocurrent response of the sensing device (blue circle) under glycerin contents ranging from 0% to 50%; (b) the instantaneous response of the GaN chip; (c) comparison with other reported work in sensing the refractive index of mediums.
Figure 12:
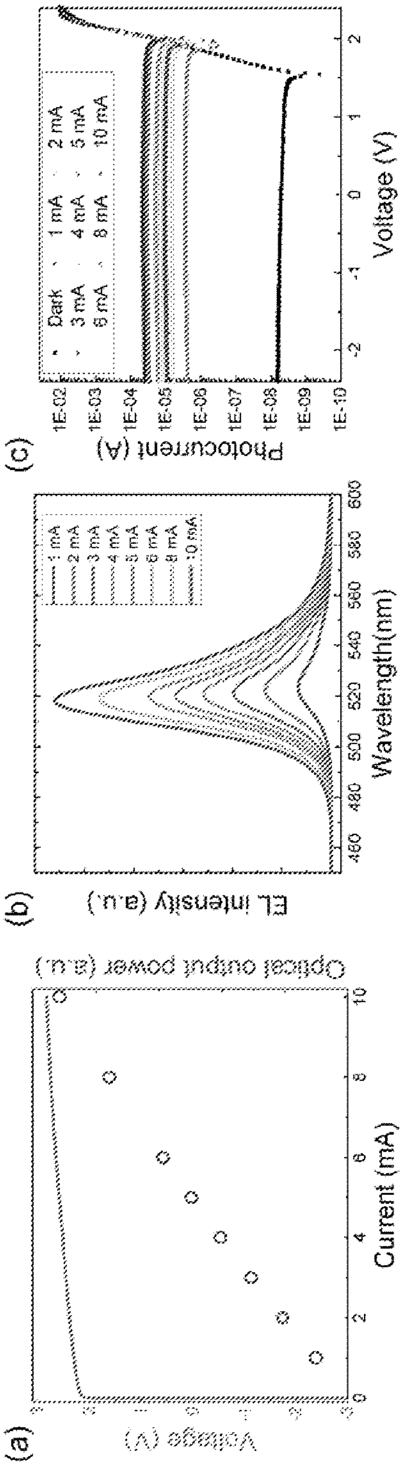
FIG. 12 depicts characteristics of the GaN chip: (a) I-V characteristics of the emitter, the inset shows the L-I characteristics of the emitter; (b) electroluminescence (EL) spectra of the LED at currents of 1-10 mA measured at room temperature; and (c) I-V curves of the detectors, the solid lines and ring-shaped symbols represent the data measured under emitters operating at 10 and 0 mA, respectively.
Figure 13:
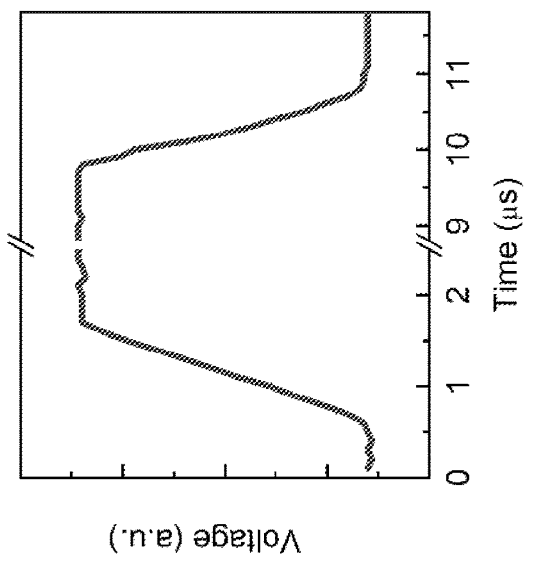
FIG. 13 depicts the response of PD when applying an impulse signal on the LED.
Figure 14:
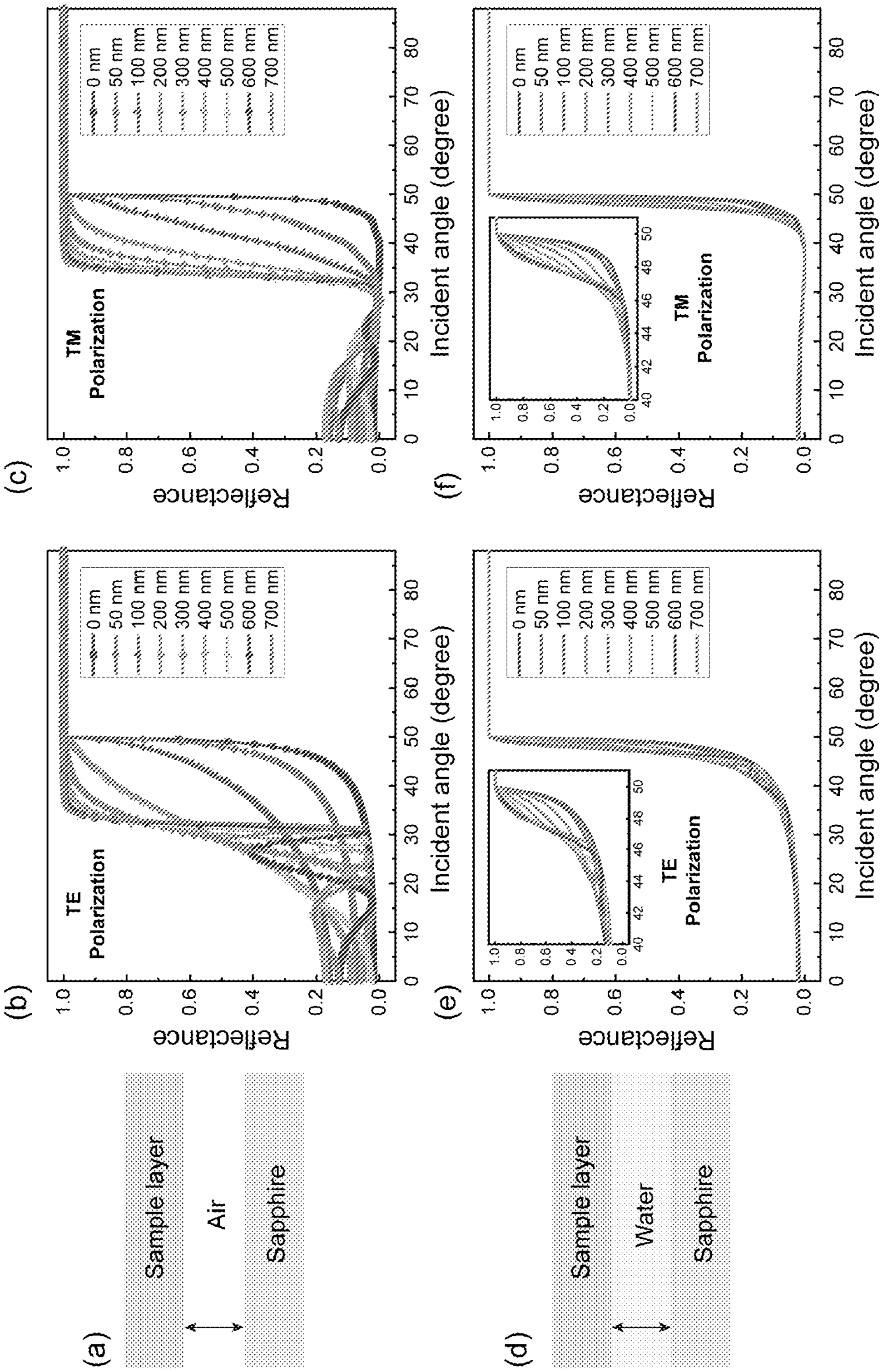
FIG. 14 depicts (a) schematic of sensing model for different thickness of air layer, and corresponding calculated; (b) TE- and (c) TM-polarized reflectance; (d) schematic of sensing model for different thickness of water layer, and corresponding calculated (e) TE- and (f) TM-polarized reflectance, the inset is the local enlarged image.
Figure 15:
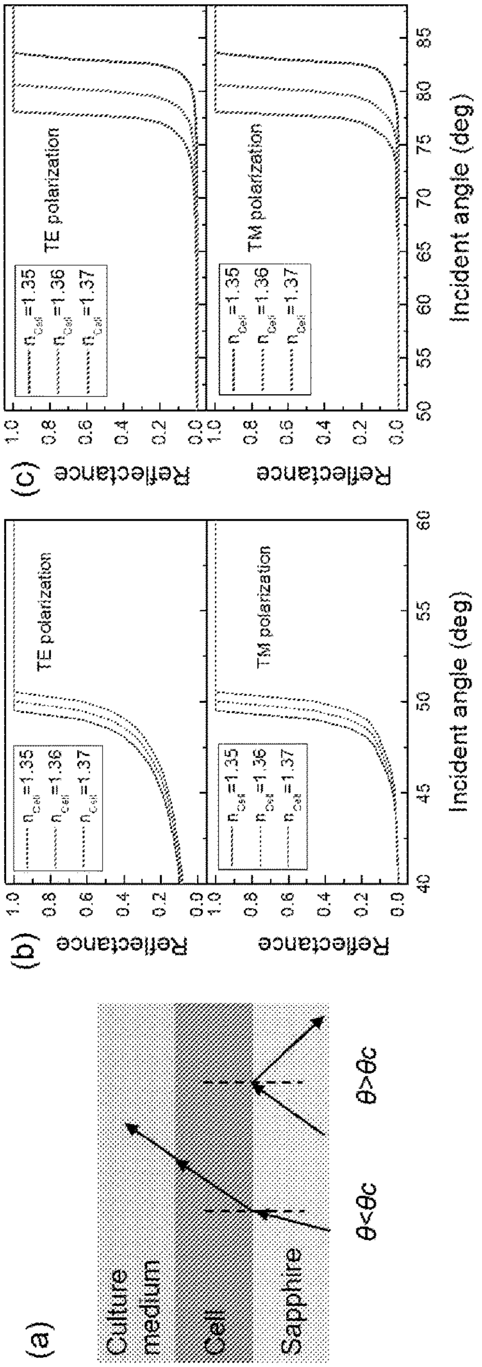
FIG. 15 depicts: (a) schematic of light propagation at different interfaces; calculated TE and TM polarized reflectance at (b) sapphire/cell and (c) cell/culture medium interfaces, respectively.

Before applying this chip device for monitoring cellular behaviors, some basic electrical characteristics of the on-chip LED and PD were conducted (See FIG. 12). Glycerin/water mixtures are used to test the sensing sensitivity, response speed, and stability of the chip device. FIG. 6*a* shows the detected photocurrent as a function of glycerin concentration, varying from 0% to 50% and therefore altering the medium RI. Extracted from the fitted linear slope, the sensitivity of the sensor is found to be around 18.93 nA/% (or 149216 nA/RIU). The sensing resolution of the chip device was found to be $2.641\times10^{-3}$%, which is determined by the resolution of the Keithley 2450 ammeter of 0.05 nA. Next, the chip response speed was quantified by a cycle test by switching the testing mediums between glycerin solution and air. The chip device responded very quickly showing only 0.169 s for the decline time T1 (from air to glycerin) and 0.386 s for the rise time T2 (from glycerin to air) (FIG. 6*b*). The rapid response time was mainly contributed to the fast photon-electron conversion property of the chip device incorporating InGaN/GaN MQWs (FIG. 13). Additionally, compared with reported methods in sensing media refractive index, this sensor exhibited a comparable sensing resolution but a much larger sensing range (RI: 1.333-1.48) (FIG. 6*c*). Herein, the theoretical sensing range will be larger (up to 1.78 of sapphire) based on the working principle of this sensor. Lastly, we conducted the simulation by building a sandwich model with sapphire-intermediate-sensing layer to characterize the vertical sensing range of the chip in water. The maximum theoretical vertical sensing ranges is 500 nm and 300 nm in water and air, respectively (FIGS. 14 and 15). The demonstration of the chip device in high sensing sensitivity, range, resolution, vertical sensing ranges and rapid response speed demonstrates its potential ability to detect more challengeable cell behaviors.

Assessing Visible Cellular Dynamics Via the Monolithic GaN Photonic Chipscope

Figure 7:
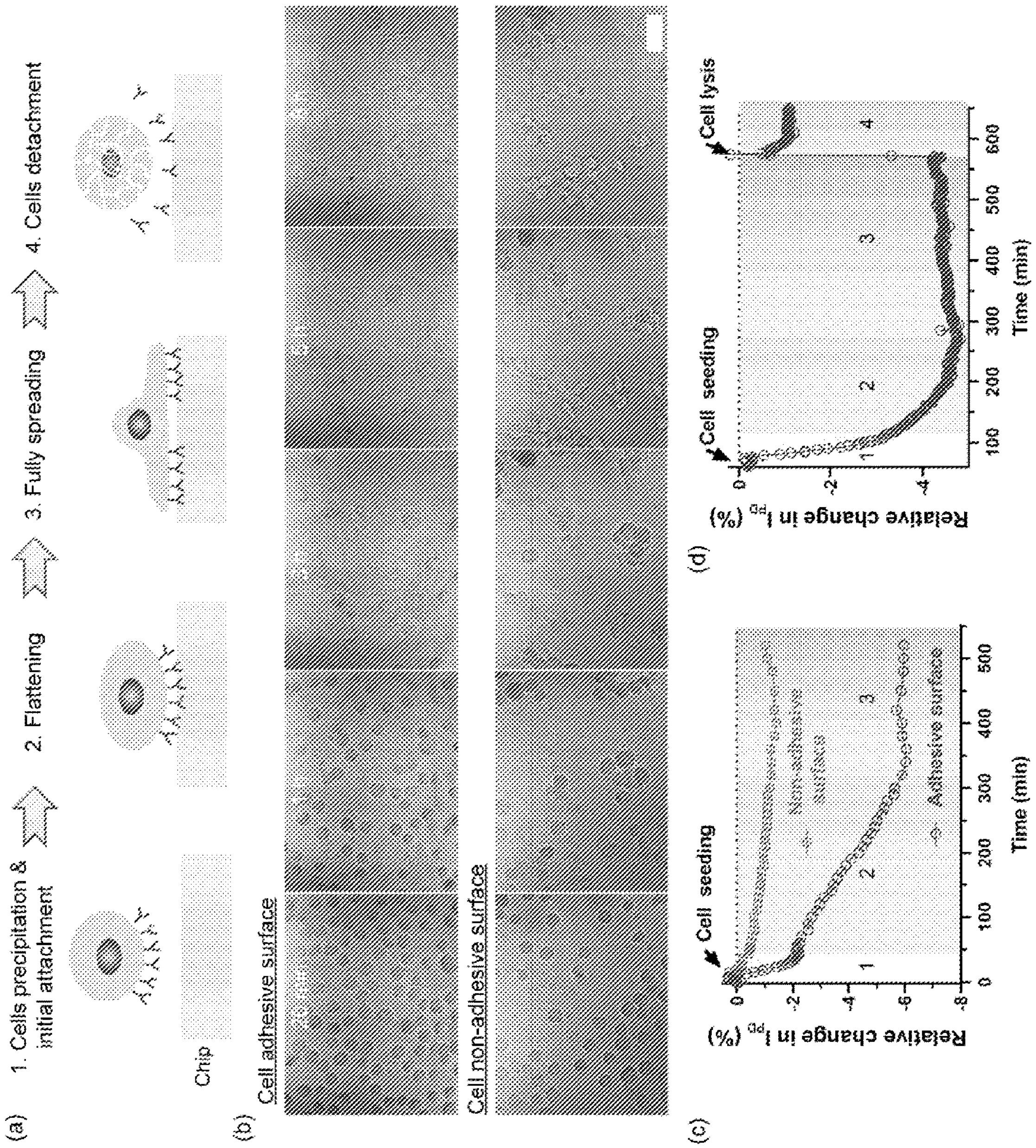
FIG. 7 depicts label-free monitoring of cell adhesion and detachment via the GaN chipscope: (a) schematic illustration of cell adhesion phases; (b) DIC images of 3T3 cells grown on the adhesive (top panel) and non-adhesive (bottom panel) surfaces from time 20 min to 8 h., scale bar indicates 100 μm; (c) relative photocurrent changes as a function of time for cells on adhesive surface (blue line) and non-adhesive surface (red line), respectively, the photocurrent data collection time interval gradually varied with time (0-1 h: 5 min/point; 1-5 h: 10 min/point; 5-9 h: 20 min/point); (d) relative photocurrent changes as a function of time for cell deposition, initial attachment, spreading, and detachment, the photocurrent data was obtained at a rate of 2 min/point (pause mode, irradiation for 5 s—pause for 115 s—irradiation for 5 s).

As a proof of concept that the GaN chipscope is capable of tracking the activities of living cells, the ability to sense cell adhesion is studied, a process that is critical for the formation of tissues and organs and participates in a large number of physiological and pathological processes, such as cell differentiation, immune response, inflammation, and tumor metastasis. In general, cell adhesion includes three steps: cell precipitation and initial cell-substrate contact, cell flattening and full spreading (FIG. 7*a*). During these processes, the main observable change is the morphological transition of the cell from being spherical to flat, resulting in a gradual increase in the coverage of cells on the chip surface. This significantly changes the average RI contrast at the cell-chip interface, thereby altering the photocurrent generated by the PD.

Figure 16:
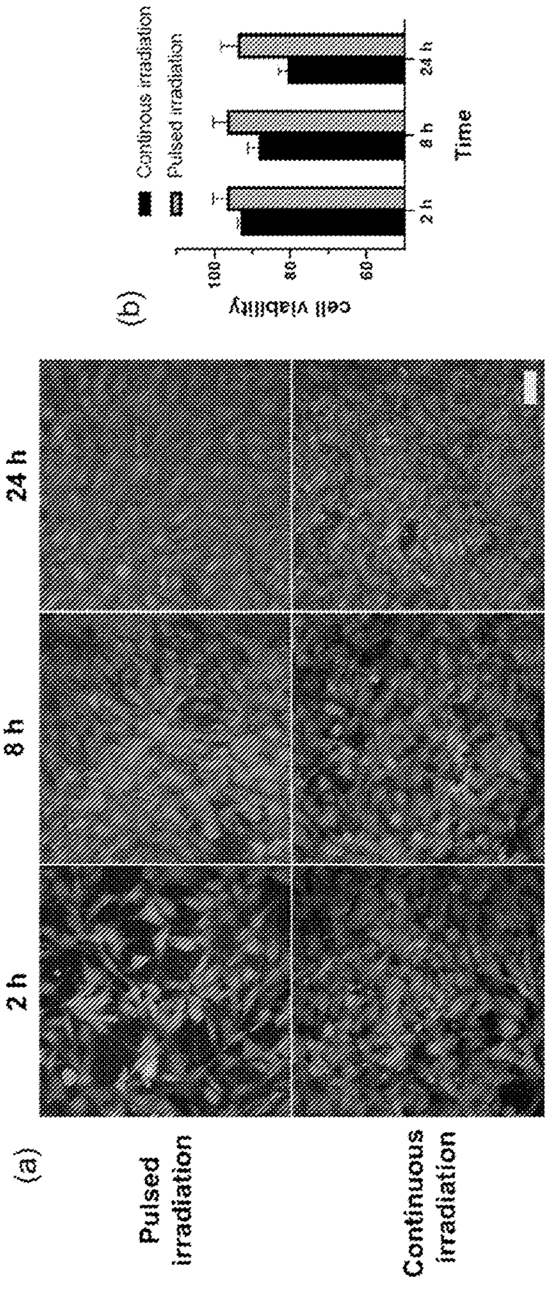
FIG. 16 depicts the cell viability study of the GaN chip for the cells, input voltage 2.4 V, input current 10 mA, pulsed irradiation: 2 min for one circle: irradiation for 5 s—pause for 115 s—irradiation for 5 s. (A) The live/dead staining of the treated cells on the chip. Green color indicates the live cells staining with calcein-AM. Red color indicates the dead cells staining with ethidium homodimer-1. Scale bar indicates 100 μm. (b) The cell viability was determined by counting the live/dead cells ratio. Data are presented as the mean±SD, (N=4-5).

NIH 3T3 cells are used in the present study due to their rapid adhesion response and significant cell area changes during spreading. First performed a live/dead assay test to evaluate the potential phototoxicity of the chip to the cells. The results showed that cells exposed to green light in both continuous and pulsed modes maintained relatively high viability (>80%) even after 24 h of treatment, indicating that our sensor chip is biocompatible for long-term cell measurement (FIG. 16). Next, after the chip was stabilized in the incubator at 37° C., the cell suspension was added into the chip chamber. Interestingly, the photocurrent dropped sharply by approximately 2.17%) in the next 30 min (despite some initial signal fluctuations), then decreased much more slowly for another 4.5 h before becoming saturated (FIG. 7*c*). Benefitting from the integrated mini-DIC imaging system, we can clearly capture the cell morphology changes in real-time. As shown in the top panel of FIG. 7*b*, the round cells gradually precipitated onto the chip surface in the first 30 min (step 1), and then started to extend in the next 4 h (step 2). After that, they continued to flatten and formed a dense monolayer sheet covering the entire chip surface (step 3). These observed cell morphology changes closely matched the optical response of the chip, indicating the successful integration of GaN chip-based sensing and DIC imaging units in our system for cellular activity monitoring. Additionally, to mimic the cell detachment process (step 4), we treated the cells with sodium dodecyl sulfate (SDS), a known surfactant that can detach and lyse adhering cells from culture dishes or flasks. Unsurprisingly, the cell monolayer became completely detached from the chip surface within a few seconds of SDS loading (figures not shown). Accordingly, the signal showed a rapid increase (4.24%) after the addition of SDS, and then slowly returned to the level corresponding to the photocurrent value before cell seeding (FIG. 7*d*). This demonstrated that our platform could not only capture the instant RI changes at the chip-medium interface, but also exhibited excellent stability for long-term measurement.

Figure 17:
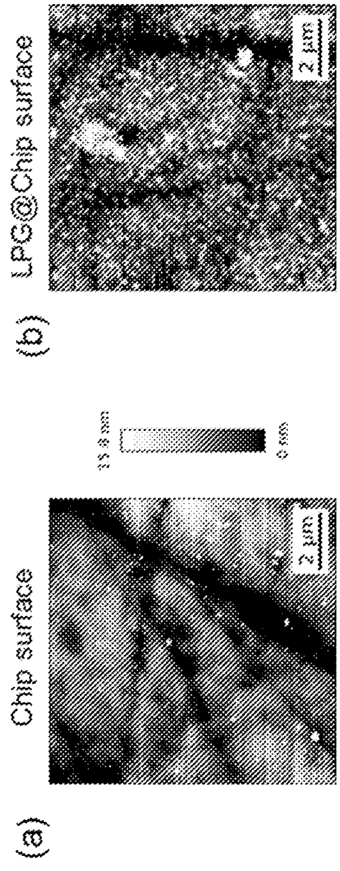
FIG. 17 depicts surface morphology of the GaN chip illustrated by the AFM: (a) bare GaN chip surface; and (b) LPG@GaN chip.

As a control experiment, we also coated the chip surface with antifouling polymers (see the detailed protocol and FIG. 17 in 11) that can effectively prevent cell-surface adhesion. Under such circumstances, cells were found to roll onto (rather than attach to) the chip surface in the first hour. Aggregation of cells took place in the next 8 hours, while no cell spreading was observed (FIG. 7*b*). Interestingly, despite a slight decrease of photocurrent by 0.55% in the first 60 min, the signal largely remained constant throughout the experiment (FIG. 7*c*).

Accessing Invisible Cellular Dynamics Via the Monolithic GaN Photonic Chipscope

Figure 8:
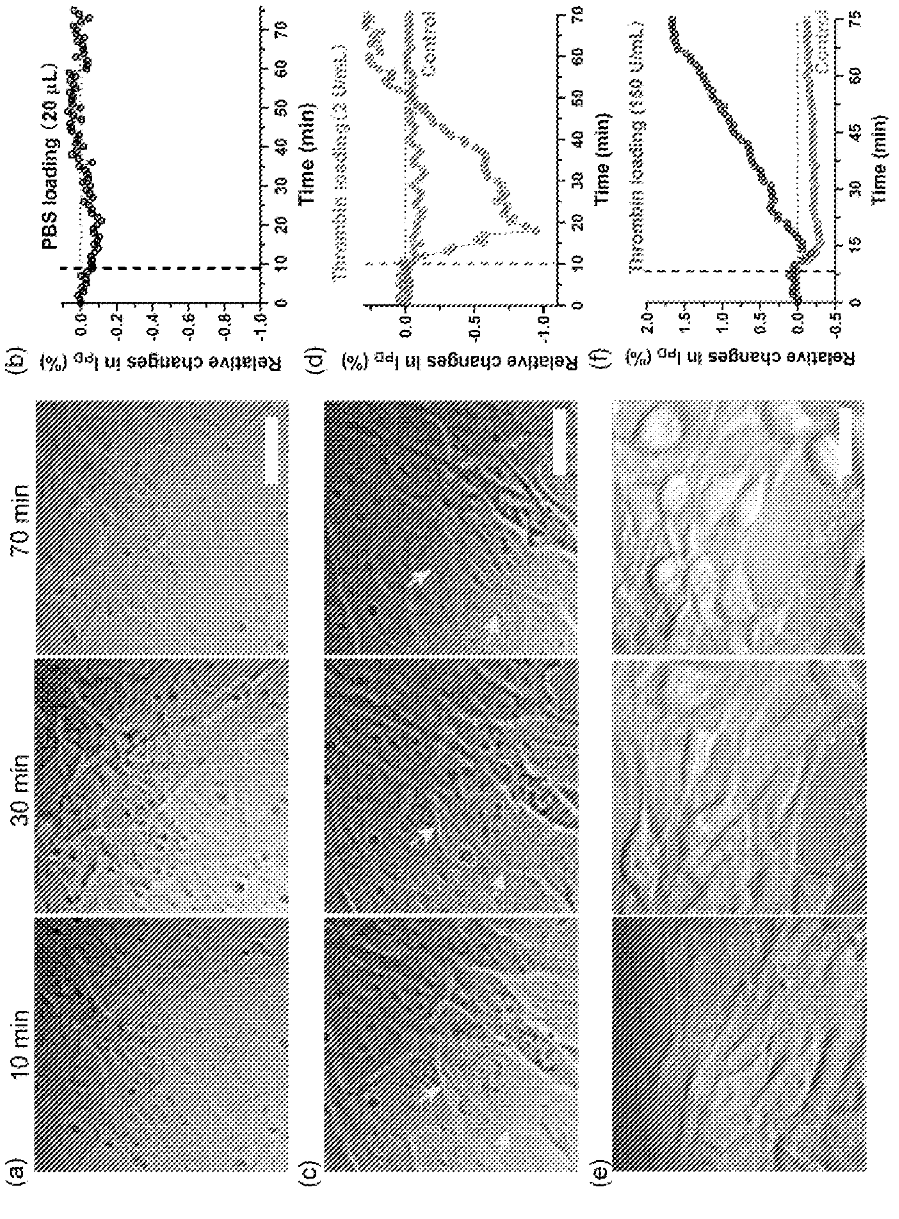
FIG. 8 depicts label-free monitoring of intracellular dynamics via the GaN chipscope: photocurrent variations as a function of time of 3T3 cells monolayer and their corresponding DIC images after stimulation by PBS (a) and (b), low dose of thrombin (2 U/mL) (c) and (d), and high dose of thrombin (150 U/mL) (e) and (f), respectively. The photocurrent data was obtained at a rate of 1 point/min (pause mode, irradiation for 5 s—pause for 55 s—irradiation for 5 s). Yellow arrows in (c) show the slight morphological changes as a result of low dose thrombin stimulation. Red dots areas in (e) represent the exposed chip surface due to drug-induced cell shrinkage. Scale bar indicates 30 μm.

To investigate the ability of the GaN chipscope to recognize intracellular dynamics, the chipscope responses under the stimulation of cells with various biomolecules and chemicals are measured and compared in FIG. 8. The photocurrent signals with DIC images taken at different time intervals after the stimulation are used to determine the morphological origin of the photocurrent signals variations. As a negative control, PBS is utilized to stimulate the cells to address the possibility of photocurrent changes being solely affected by the interference from the liquid shear force in the chip chamber. As expected, no apparent variations in the photocurrent signal are observed after the PBS was loaded (FIG. 8*a*). The imaging unit confirmed this result, showing no detectable change in the cell morphology (FIG. 8*b*).

Figure 18:
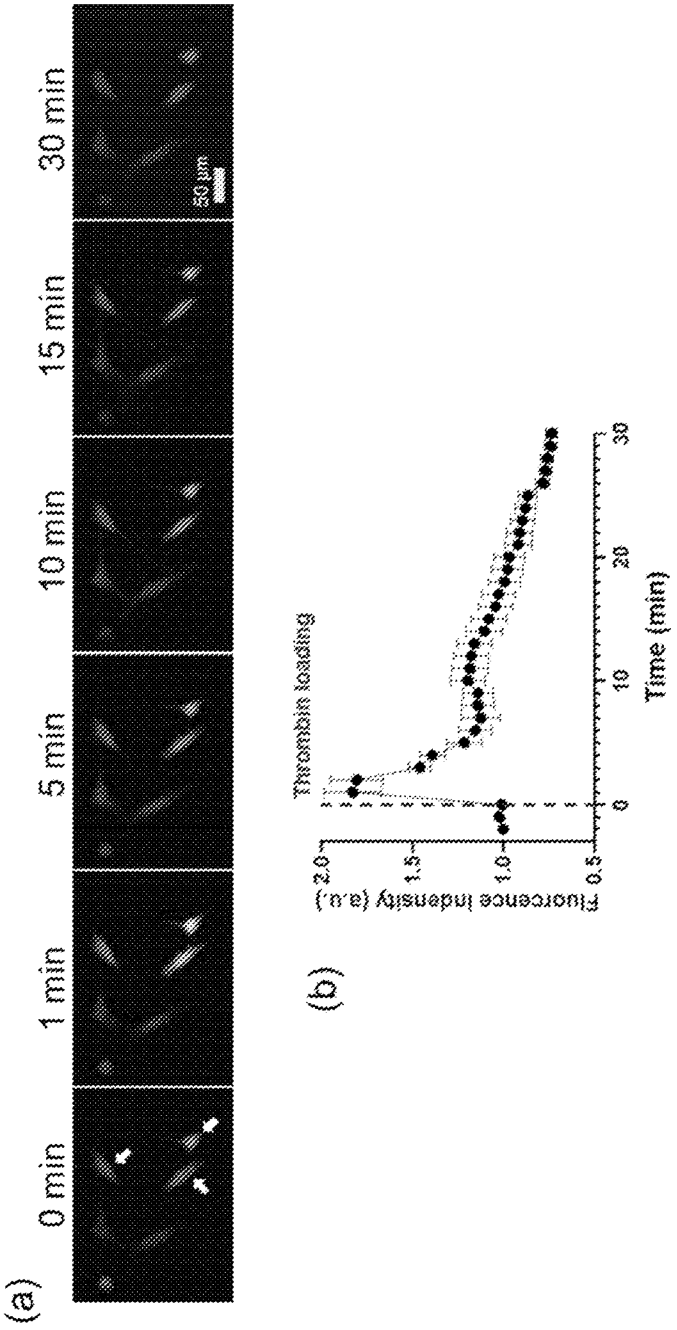
FIG. 18 depicts living cell calcium tracking after the loading of low dose of thrombin: (a) The time laps fluorescent images of the calcium (green) in living cells (thrombin 2 U/mL); and (b) the calcium fluorescence intensity was quantified. Data are presented as the mean±SD, (N=3).

Next, the cells were stimulated with thrombin at two different doses. Thrombin is a serine protease that is well known to be implicated in hemostasis and vascular endothelium permeability. Actually, cells can interact with thrombin through the thrombin receptors, which have been identified on many types of cells, including endothelial cells, smooth muscle cells, neuronal cells, fibroblasts, and peripheral blood lymphocytes, etc. A low dose of thrombin has been shown to temporarily increase the internal elastic tension by enhancing the activity of the $Ca^{2+}$ based myosin light chain. By contrast, a high dose of thrombin is toxic and induces cell death by cleavage of DNA into fragments. As shown in FIG. 8, after stimulation with a low dose of 2 U/mL thrombin, the cells showed a biphasic response. In the first 10 min, the signal dramatically decreased (0.94%), probably as a result of the increase in RI induced by the sharp increase in intracellular $Ca^{2+}$ concentration after thrombin (low dose) loading. In the next 30 min, the signal returned to its initial level. Since the working time of thrombin is within a range of minutes, the local concentration of $Ca^{2+}$ gradually returned to the normal state, resulting in a recovery phase of photocurrent in the following 30 min. The result is further confirmed by a living cell calcium tracking experiment, where a similar biphasic cell response is observed in the presence of low-dose thrombin. This result perfectly matched the data recorded by the GaN chipscope (FIG. 18). Importantly, the cell spreading area and cell morphology monitored by the imaging system showed no visible changes, and there was only slight cell extension after thrombin treatment (yellow arrows labeled, FIG. 8*c*), indicating that the intracellular dynamics dominate the photocurrent generation.

We then increased the dose of thrombin to 150 U/mL and observed a rapid increase of photocurrent throughout the tested period. The photocurrent reached a plateau after 50 min and then stabilized, with a maximal change of 1.66% (FIG. 8*f*). Consistent with the photocurrent data, the imaging unit monitored an increase in the intercellular space due to cell shrinkage induced by thrombin (FIG. 8*e*). In this case, the cell spreading area and optical current data are negatively correlated with each other. To corroborate this result, blebbistatin is used to induce the cell morphology changes by inhibiting the myosin II activity. Myosin II is a critical determinant of contractile characteristics of cell motility and cell adhesion in several tissue types. After treatment with the drugs (50 μM), the cells gradually shrank in the next 1 h, showing increased cell gaps and dendritic cell morphologies (FIG. 3*a*). As expected, an increase in photocurrent is observed during this period due to the decrease of the cell coverage area on the chip surface (FIG. 3*b*).

Cells can respond to chemical stimuli in a variety of ways, including the activation of signaling pathways, morphological changes, and the initiation of cell death. The currently available systems on the market for label-free and real-time monitoring of cells in vitro are mostly based on cell morphology/cell spreading, which means that the cell activities can only be measured when there are cell morphological changes or cell spreading variations. Herein, the newly developed GaN chip is able not only to measure changes in cell morphology/cell spreading, but also to sense and record RI dynamics induced by intracellular dynamics in real-time. It is even capable of determining the dominant factor contributing to the RI changes with the help of the imaging analysis. These unique features make the GaN chipscope an excellent candidate for monitoring cell response against various drugs and chemicals in vitro in a variety of ways.

GaN Chipscope in the Demonstration of Drug Screening

Figure 9:
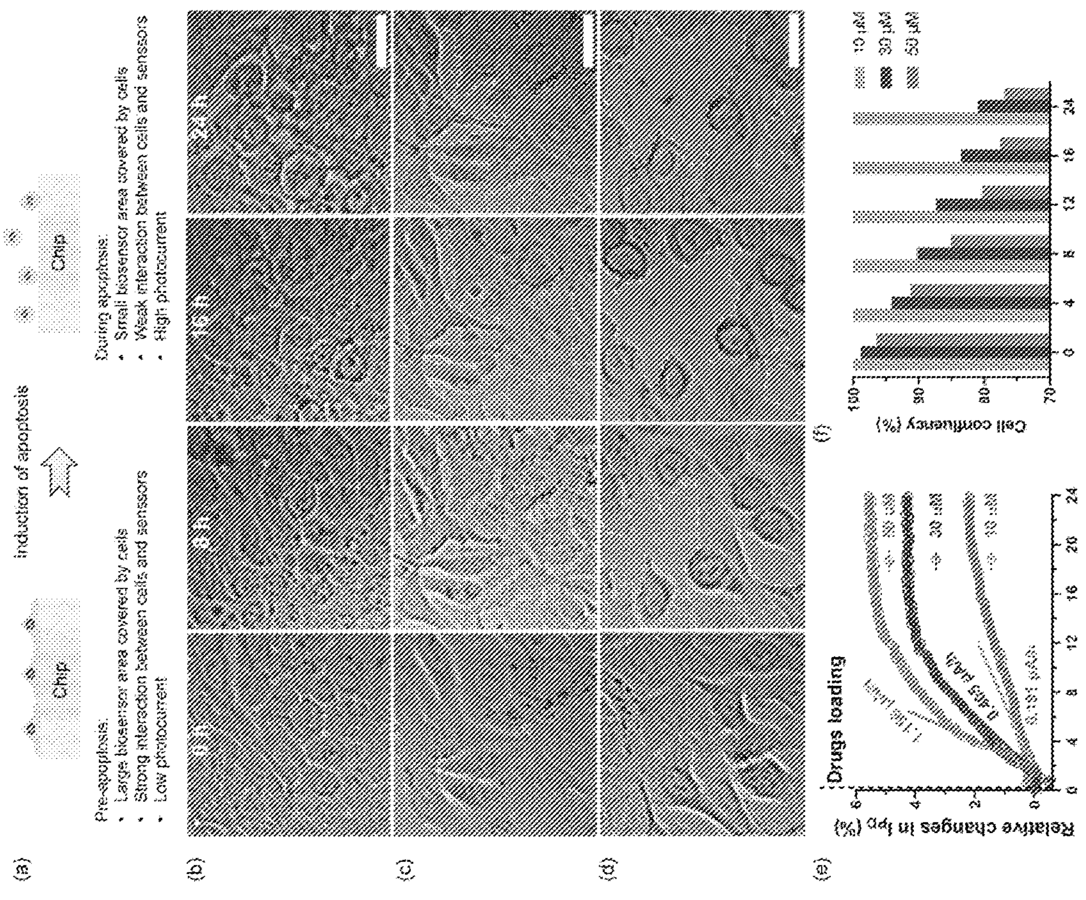
FIG. 9 depicts GaN chipscope in the application of drug-cell interactions: (a) schematic illustration of drug-induced cell apoptosis; representative images of A549 cells treated with anticancer drugs with varied concentrations at specific timepoints (b) 10 μM, (c) 30 μM, (d) 50 μM. (e) photocurrent variations as a function of incubation time (A549 cell monolayers treated with drugs with varying concentrations). The solid lines represent the liner fitting to the data. The photocurrent data was obtained at a rate of 10 min/point (pause mode, irradiation for 5 s—pause for 595 s—irradiation for 5 s); and (f) the cell confluency variations as a function of the drug stimulation time and dose.

To demonstrate the potential application of this sensing platform in drug research, an experiment is conducted to determine the cytotoxicity of the anticancer drug β-lapachone on human lung adenocarcinoma cells (A549). The A549 cells are seeded in the chamber of the platform and cultured for 24 h for fully spreading. Afterward, 10 μM, 30 μM or 50 μM of β-lapachone is added into the chambers, respectively. As shown in FIG. 9, the chipscope recorded the responses of A549 cells stimulated by β-lapachone. Clearly, the β-lapachone induced dose-depend cytotoxicity in A549 cells, as characterized by a significant increase in the photocurrent data with increasing drug concentration.

Additionally, the photocurrent curves offered valuable practical information for the study of drug-cell interactions. First, by plotting the slope of the tangent line, the speed of cell response at different periods was analyzed. For instance, in the first 5 h of stimulation, the response exhibited by the cells at a high β-lapachone concentration (50 μM) was 6.05 and 2.85 times higher than that at low (10 μM) and intermediate concentrations (30 μM), respectively (FIG. 9*e*). Secondly, the photocurrent curves revealed the reaction time of the cells under different drug concentrations. For instance, A549 cells exhibited a much faster response against a high dose of β-lapachone (12.5 h and 11.6 h for 50 μM and 30 μM of β-lapachone, respectively) than against a low dose (20.2 h for 10 μM of β-lapachone). Indeed, a higher dose is more toxic and induces faster cell death. Thirdly, by coupling the imaging system, we were able to qualitatively and quantitatively analyze the cell-drug interactions. As shown in FIG. 9*b-d*, the cells shrank in a dose-dependent manner after β-lapachone treatment. Specifically, cells treated with a lower dose (10 μM) slowly shrank over time, but there is no obvious increase in intercellular spaces during the 24 h. This suggested that the photocurrent dynamics are mainly to be ascribed to the intracellular RI changes induced by the drugs instead of to the changes in the cell spreading area. The A549 cells treated with higher dose of β-lapachone shrank intensely and showed significant intercellular gaps (red dots line labeled) in the intermediate and high dose groups (FIGS. 9*c* and *d*). It is believed that the increase in photocurrent in higher dose-treated cells is contributed by both cell morphology changes as well as by cell intracellular dynamics alternation. Further, the cell confluency is calculated based on the photos taken by the imaging system. As a result, the confluence of cells treated with high, medium, and low doses of β-lapachone decreased by 23.1%, 19.0%, and 0%, respectively after 24 h incubation.

Therefore, this GaN chipscope platform is capable of recording cell response in regard to both cell adhesions and intra-/intercellular dynamics after drug treatment, demonstrating its practicality as a toxicity biosensor in rapid drug screening studies.

Demonstration of Cell Differentiation Monitoring

The cell refractive index is an intrinsic optical parameter that varies with different cell phenotypes. This inspired the exploration of whether the sensing platform could track online the dynamics of cell differentiation and distinguish the different cell phenotypes. In this experiment, human monocytic THP-1 cells are employed as the cell model due to their multi-phenotypic characteristics, including the initial suspended monocyte, adhered macrophage (M0), and two major polarized states (adhered M1 and M2). Here, THP-1 cells differentiated from suspended state (monocyte) to adhered M0 state by phorbol 12-myristate 13-acetate (PMA), followed by induction of the resultant M0 cells to polarize to M1 by LPS/FN-gamma. The process is monitored throughout by the GaN chipscope system (FIG. 10*a*).

Figure 10:
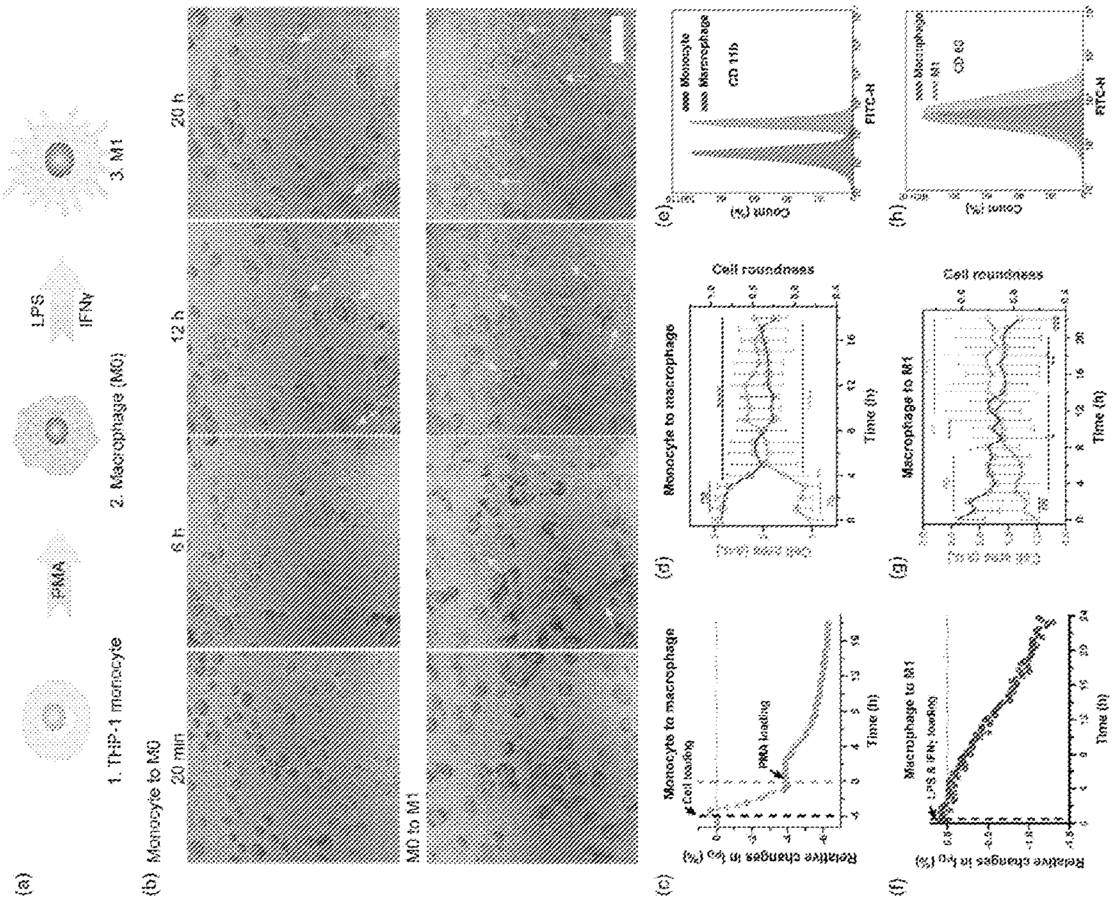
FIG. 10 depicts GaN chipscope platform applied in cell differentiation monitoring: (a) Schematic illustration of differentiation of THP-1 monocyte to macrophage with different phenotypes; (b) representative images of monocyte differentiate to M0 cells (upper panel) and M0 cells differentiate to M1 cells (bottom panel), respectively. Scale bar indicates 100 μm; (c-d) the relative changes of optical current, cell area, and cell roundness as a function of time during monocyte to M0 differentiation (n=20-30); (e) the specific macrophage surface marker CD 11b expression is illustrated by flow cytometry analysis; (f-g) the relative changes of optical current, cell area, and cell roundness as a function of time during M0 to M1 differentiation (n=20-30); (h) the specific M1 surface marker CD 80 expression is illustrated by FACS analysis. The photocurrent data was obtained at a rate of 15 min/point (pause mode, irradiation for 5 s—pause for 895 s—irradiation for 5 s). Cell images were analyzed using Image J (NIH). For quantification of cell spreading area, the shape factor and fluorescent intensity of each cell was readily obtained from Image J measurement). Data are presented as the mean±SD, n=20-30. All data were compared with control group at the time 0. P-values<0.05 were considered statistically significant (*p<0.05, p<0.01, *p<0.001).

The photocurrent signal slightly decreased after monocytes are seeded into the chip chamber, indicating that these cells precipitated onto the chip surface due to gravity (FIG. 10*c*). Consistent with the photocurrent signal, the imaging system recorded a fast cell rolling behavior in the initial 30 min before the cells settled down (FIG. 10*b*). PMA (25 ng/mL) is then loaded to trigger monocyte to macrophage differentiation. It is evident from the photocurrent signal that monocytes responded strongly against PMA in 3-9 h after stimulation, and this response became mild in the following 11 h (FIG. 10*b*).

The cell spreading area is calculated according to the photos taken by the imaging system. It is slightly increased in the first 3 h, followed by a significant increase (137%) in cell area in 3-9 h, but fluctuated in the following 11 h. In contrast, the cell roundness exhibited a trend opposite to the cell area (FIG. 10*d*). It is noticed that the imaging data perfectly matched the photocurrent dynamics during the first 9 h after PMA stimulation, which indicated that the photocurrent signals are mainly contributed by the adhesion-based cell area changes and intracellular dynamic. In the following 10-20 h, the photocurrent data kept decreasing, but the cell area shows no noticeable change, indicating that the cell-intrinsic property dynamics dominated the signals in this period. To confirm the differentiation of monocyte to macrophage, CD11b as a macrophage surface marker is evaluated by flow cytometry and immunofluorescence staining. After incubation with PMA, the expression of CD11 b of THP-1 cells is significantly increased (FIG. 10*e*), indicating the successful differentiation of monocyte to M0.

To polarize M0 to M1, macrophages were treated with lipopolysaccharide (LPS, 100 ng/mL) and interferon-gamma proteins (IFNγ, 20 ng/mL). A steady decrease of the photocurrent signal is observed in the 24 h following stimulation (FIG. 10*f*). Similarly, the cell spreading area gradually increases by 87% within this 24 h, and the polarized cells showed a "dendritic"-like morphology with large filopodia (arrows labeled, FIG. 10*b*). By contrast, cell roundness decreases from 0.3 to 0.57 (FIG. 10*g*). There is apparent shifting of M1 macrophage surface maker CD 80, which confirmed the successful differentiation of M0 to M1 macrophage (FIG. 10*h*). Together, these results indicate that our GaN chipscope can monitor in real-time and quantify cell activities or status changes in both intracellular and intercellular dynamics. Additionally, this device integrated with an imaging system is label-free and incubator-adaptive, making it highly suitable for various tests and analyses in living cells in situ.

Some Conclusions

Here, introduce is a low-cost, incubator-adaptive chipscope based on the refractive index-sensitive GaN device for label-free and real-time cell sensing. The device benefits from its small size, continuous monitoring, and real-time photocurrent readout and analysis, enabling us to readily capture the dynamics of cell adhesion-based activities in situ, including cell precipitation, initial attachment, spreading, shrinkage, and detachment. In particular, by coupling the imaging unit and RI sensing unit, the platform can determine both intercellular and intracellular dynamics by monitoring the cell adhesion and morphologies changes with high sensitivity and responsiveness. Another specific outcome of this work is the development of a practical, ready-to-use cell analyzer for pharmacological studies to determine the cytotoxicity of anticancer drug and their corresponding cellular response, as well as cell biology research to track the immune cell phenotypes transform. Technically, these results are sufficiently robust to demonstrate the applicability of the optical chip-based sensing technology in biosensing.

Compared to the prevailing complex optical living cell biosensing technologies, such as SPR and RWG, our GaN chips tremendously lower the technical thresholds in the design, fabrication and the practical use of biosensors (Table in FIG. 19). Specifically, the monolithic strategy was utilized to integrate InGaN/GaN photo emitter and photo detector on the same microchip, which eliminate the use of the costly spectrum analyzer and other optical apparatus. Additionally, due to their microscale size and the less requirement on the sensing setup, the chip can be easily integrated with other devices and applied in some special environments such as fast detection in the wearable device, integration with microscope or working in tight space with high humidity (cell incubator).

The GaN chipscope platform can be used as a tool for label-free monitoring of live cell activities which transcends the boundaries of the conventional "photonic chip" and "microscopy" monitoring processes. The new chipscope integrates more functions that highly enrich the data output in both qualitative and quantitative ways. In particular, their easy accessibility and extremely low manufacturing cost (<10 cents per chip) may enable them to be welcomed in the practical use and the market.

Described herein is a versatile, incubator-compatible, monolithic GaN photonic chipscope for label-free monitoring of live cell activities. Regarding the electrical characteristics of the photonic chip, as shown in FIG. 12*a*, the I-V curve illustrates that the measured forward voltage of LED is 2.4 V at 10 mA, and the resistance obtained based on the slope of the linear region is 4.95Ω. Also, the output power of the LED was linearly proportional to the input current. Not surprisingly, as the injecting current in LED increased, the electroluminescence intensity became larger, as shown in FIG. 12*b*. However, a fixed low input current of 10 mA was used in all our experiments to avoid possible phototoxicity to living cells. FIG. 12*c* shows the I-V curve of PD under a reverse bias voltage where photocurrent generated by the photodetector was kept at a high level of $10^{-6}$ to $10^{-4}$ A (in contrast to that of $\sim 10^{-8}$ A without illumination) when the LED injecting current increased from 1 mA to 10 mA. This demonstrates that the measured data possess a high peak signal-to-noise ratio (PSNR).

Additionally, the chip response time is determined by injecting an electrical pulse into the LED. The LED-converted optical pulse signal is received by a PD connected to a transimpedance amplifier and an oscilloscope. From the measured result shown in FIG. 13, our chip can provide fast transition times, with the rise and fall times below 1.5 s, which was mainly contributed to the fast photon-electron conversion property of the chip device incorporating InGaN/GaN MQWs.

Determination of the Vertical Sensing Range of the GaN Chip.

To determine the vertical sensing ability of the GaN chip, the simulation is conducted by building a sandwich model with sapphire-intermediate-sample layer to characterize the vertical sensing range of the chip. Two possible cases are defined: (1) the vertical separation between the chip and targeted sample layer, and (2) the vertical distance that can be sensed by the chip in the targeted sample layer.

The simulation is conducted by a commercial FEM simulation software, known as COMSOL Multiphysics. Particularly, a sandwich model composed of sapphire/cell/culture medium layers is conducted, and the model construction and solving are in the 2D Wave Optics module. Plane-wave with different incident angles and one-unit cell by applied periodic boundary conditions are performed herein. The refractive indexes of the sapphire and culture medium are fixed at 1.78 and 1.34, respectively, while the refractive index of the cells is set to a range of 1.35-1.37.

Case 1: it is supposed the targeted sensing layer as the monolayer cells. When the intermediate between the chip and sensing layer is air, the total reflectance (internal reflectance and scattering) responds to a limited distance ranging from 0 nm to 300 nm (FIGS. 14*a* and *b*). When the intermediate medium changes to water, the vertical responsive distance is 0-500 nm (FIGS. 14*c* and *d*). Therefore, the theoretical maximum vertical sensing range will be around 300 nm and 500 nm for air and water, respectively.

Case 2: the degree of reflectance is governed by the refractive index difference at the interface. During the cell detection process, there exist two interfaces (sapphire/cell and cell/culture medium) above the chip, as illustrated in FIG. 15*a*. When the incident angle exceeds the critical angle (θc=~50°) at the sapphire/cell interface, the light undergoes total internal reflection, as shown in FIG. 15*b*. Only light rays with an incident angle less than the critical angle partially enter the cell. However, the weak refractive index contrast at the culture medium/cell interface leads to a large critical angle of >78°, as illustrated in FIG. 15*c*. Moreover, the culture medium/cell interface provides very weak reflectance, and the amount of light that can be reflected is highly limited.

During measurements, it is expected that the lateral spreading of the cell across the chip surface can increase the amount of reflected light at the culture medium/cell interface. However, the photocurrent magnitude is found to decrease monotonically over time, implying that reflected light from this part is negligible. As such, light undergoing total internal reflection at the sapphire/cell interface remains the dominant part.

Fabrication of the Cell Adhesion-Resistance Surface on the GaN Chip

To establish a cell adhesion resistance surface on the GaN chip, a monolayer polymer coating based on liner polyglycerol (LPG) is employed in this work, which has been proved capable of providing effective antifouling properties in various substrates. The fabrication of the antifouling polymer layer on the device is via two steps: 1) a hydrophobic layer is formed on the sapphire surface of the device by sialyation; 2) amphiphilic block copolymers benzophenone functionalized liner polyglycerol (LPG-BPh) self-assemble on the alkyl-functionalized substrates through the hydrophobic-hydrophobic interaction between the hydrophobic domain (BPh) of the polymer and hydrophobic base alkyl layer. Then, the polymers were covalently bonded on the alkylated sapphire by the UV initiated "C—H" photo-crosslinking between BPh groups and neighboring "C—H". The thickness of the monolayer coatings is about 3.5 nm. FIG. 13 shows the surface morphologies of the sapphire face of the device without and with the LPG coating. The island-like pattern from FIG. 13*b* corresponds to the surface feature of monolayer polymer brush coating. In addition, no significant changes in the roughness can be observed after the surface engineering (bare chip: $R_a$=3.46 nm, LPG @chip: $R_a$=3.15 nm).

Hydrophobic layer establishment on the chip surface: the cleaned chips were actived by the surface plasma, and then were immersed in ethanol solution containing 30% v/v acetic acid and trimethoxy-(octyl)silane (0.5 M, for octyl substrate) in a big-neck flask. The flask was placed at room temperature for 1 day. After that, the slides were thoroughly rinsed by ethanol and dried with $N_2$ stream.

Antifouling coating preparation: The antifouling coating is prepared via a simple one step dip-coating method. The cleaned octyl substrates were dip into a solution of 1 mg/mL LPG-BPh in Milli-Q water at room temperature for overnight. After that, the coated chip were thoroughly rinsed with water and dried by $N_2$ stream.

Surface characterization: AFM data was got by a NanoWizard 4XP scanning probe microscope (Bruker, USA) in air. The images were got from AC Mode with commercially available AFM cantilever tips (TESP-V2, Bruker) with a spring constant 42 N/m.

Unless otherwise indicated in the examples and elsewhere in the specification and claims, all parts and percentages are by weight, all temperatures are in centigrade, and pressure is at or near atmospheric pressure.

Results (on Ensemble Cells)

1. Experiments Methods:

Cells (NIH 3T3, 0.3 million/mL, 500 uL, 37° C.) were seeded on the LED chip and transferred to the incubator (37° C.). Then the ammeter started to monitor the optical current at specific time points. The control experiment was performed by monitoring the solo cell culture medium with an identical chip (DMEM, 500 uL, 37° C.).

The bright-field images of cells were collected at specific time points to monitor the initial stage of cells adhesion and extension. The cells were cultured on sapphire, the substrate of which was identical with the top layer of LED chips.

2. Results and Discussion

Before the cell seeding, the chips with culture medium were stabilized in the cell incubator for 4 hours to monitor any noise from the environments (temperature, humidity, light, etc.) during the detection. The current signals of both control group and experimental group were quite stable (FIG. 1*c*). After the cells seeding, the optical current of experimental group experienced an obvious decrease of 9.91% (0.3287 μA) in the first 2 h and almost no signal changes from the control chip (−0.39%). It is assumed that it might be contributed to the refractive properties changes during the cell deposition on the surface. To prove this, optical images were collected at specific time points and showed that most of cells deposited on the chip surface in the first 2 hours (FIG. 1*d*). At the time of 3 h, cell started to spread and highly extended at time of 8 h (FIG. 1*d*).

Interestingly, a slight increase of 2.263% of optical current was observed during this time range. It is believed that it is the cell spreading that led to the increase of the optical current after hour 3. In addition, it indicated that the tiny refractive properties changes induced by cell adhesion from round morphology to flatten morphology could be successfully monitored by our LED chips.

Importantly, the performance of control group (culture medium) is quite stable during the whole experiment (FIG. 1*c*). Together, these data fully demonstrated that our LED chips are very sensitive and reliable for the detection of cellular activities in such the complex cell culture conditions with high humidity, salinity and biofouling.

Fabrication of the Optoelectronic Chip:

The epitaxial structures containing InGaN/GaN multi-quantum-wells (MQWs) were grown on a 4-inch sapphire substrate by metal-organic chemical vapor deposition. The LED and PD mesas were then fabricated on a single wafer by photolithography and inductively coupled plasma (ICP) etching. In order to promote the spreading of current, a 120 nm-thick indium-tin-oxide (ITO) layer was deposited on the p-GaN by reactive plasma deposition. The LED and PD were covered by photomasks and a 10 μm-wide GaN between them was then ICP-etched. The p-electrode and n-electrode were subsequently patterned by photolithography and then coated with Cr/Al/Ti/Pt/Au materials by electron-beam evaporation. An insulating $SiO_2$ layer with 360 nm thickness was deposited on the wafer by plasma-enhanced CVD technique. A stacked layer of $SiO_2/TiO_2$ distributed Bragg reflector was deposited as a bottom mirror to reflect the emitted light into the sapphire substrate. The p-pad and n-pad regions were defined by photolithography, and a metallization layer was then deposited by electron-beam evaporation. After rapid thermal annealing, the sapphire substrate was thinned to 150 μm by lapping and polishing process, followed by laser dicing into small chips with the size of 1×1 $mm^2$. Both LED and PD possess the same device structure, as shown in FIG. 5*c*.

Construction of a mini-differential interference contrast (DIC) microscopy: A green GaN chip with an emission wavelength of 520 nm was employed as the light source, and the diffused light beams were further modified through a focal lens. The modulated parallel light propagated through a polarizer and became linearly polarized. After beam splitting, the separated downward beams passing through a birefringent Normarski prism were collected with a 40×DIC objective with 0.6 NA, and then irradiated on the specimen. The reflected wavefronts experienced varying optical path differences due to irregular specimen surface topography and were gathered by the objective and focused on the interference plane of the prism. The combined lights continued to propagate through the beam splitter and then encountered the analyzer (second polarizer), which allowed the light beams parallel to the analyzer transmission vector to pass through, further undergoing interference and generating amplitude fluctuations at the focal plane of the lens. Finally, the DIC image was captured by a CMOS camera (Thorlabs).

Cell Culture:

NIH 3T3 cells and A549 cells were purchased from ATCC and cultured in DMEM (Gibco) supplemented with 10% bovine growth serum (Gibco) and 1% penicillin/streptomycin (Gibco). NIH 3T3 cells between 6-12 passages were used in this study. A549 cells between 4-10 passages were used in this study. THP-1 cells were purchased from ATCC. The cells were cultured in RPMI 1640 (Gibco) medium supplemented with 10% heated-inactivated bovine growth serum and 1% penicillin/streptomycin (Gibco). THP-1 cells between 10-15 passages were used in this study. All cells were cultured at 37° C. with 5% $CO_2$ and passaged twice a week according to the standard protocols.

Cell Viability Test:

3T3 cells were seeded at 100000/$cm^2$ on the chips. After a pause of 24 h to permit the cells to fully spread, the chips were activated in two modes: continuous mode (input voltage around 2.4 V, input current 5 mA, continuously irradiation) and pause mode (input voltage around 2.4 V, input current 5 mA, 2 min for one circle: irradiation for 5 s—pause for 115 s—irradiation for 5 s). After the cells were treated several times, they were washed with PBS, and incubated with a live/dead assay (Thermo) in incubator for 30 min. The fluorescence images were then captured by microscopy, and the live/dead ratio was determined through imaging by counting the number of live and dead cells.

Cell Differentiation and Characterization:

Phorbol-12-myristate-13-acetate (PMA, MCE, 25 ng/mL) was used to induce monocytes differentiation to M0 macrophages. For further polarization, 100 ng/mL lipopolysaccharide (LPS, Thermo) and 20 ng/mL interferon-γ (IFN-γ, Thermo) were added to the culture to induce M1 generation. The cells were stimulated to M0 and M1 macrophages for 24 h. Flow cytometry and immunofluorescence staining were used to assess the expression of macrophage-specific cell surface marker: CD11 b for monocyte/macrophage differentiation and CD 80 for M1 macrophage polarization.

Thrombin Stimulation Study:

3T3 cells were grown on the chip surface for overnight and then were washed once and replaced with HEPES buffer (HBSS). After the system was restabilized, various concentrations of thrombin (MCE) were injected into the cell chamber. The signal dynamics were recorded by a meter.

Living Cell Calcium Tracking:

After the cells were grown on the confocal dish for 24 h, they were washed by PBS and cultured in living cell fluorescence imaging medium (Thermo) with the calcium indicator (Fluo-3, Invitrogen, 5 μmol) and pluronic F-127 (0.02%) in incubator for 1 h. They were then washed by fresh culture medium twice and incubated for a further 30 min to allow complete de-esterification of intracellular acetoxymethyl esters. The living cell fluorescent images were then captured by fluorescence microscope (Zeiss) with the frame rate of 1 side/min.

Flow Cytometric Measurements:

The harvested cells were washed with cold PBS and then the Fc receptor binding sites were blocked by incubating with Human TruStain FcX™ (422302, Biolegned) on ice for 20 min. The cells were then incubated with either FITC labeled CD 11 b (301329, Biolegend) or FITC labeled CD 80 (305206, Biolegend) in darkness for another 30 min. After centrifugation, the cells were washed twice with FACS buffer (PBS containing 2% BSA) and immediately measured by the flow cytometer Novoexpress (Agilent).

Statistical Analysis:

Statistical analyses were performed with GraphPad Prism 8, with statistical significance set at $P<0.05$ (*$p<0.05$, $p<0.01$, *$p<0.001$). Data are represented as mean±standard deviation (S.D). One-way analysis of variance (ANOVA) followed by posthoc Tukey's multiple comparisons test was carried out for group differences.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention is explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. An integrated sensing and imaging system, comprising:
- a monolithic optoelectronic chip;
- a first prism; and
- a constructed miniature optical imaging module for differential interference contrast microscopy, including a second prism,
- wherein the monolithic optoelectronic chip comprises a light-emitting diode and a photodiode positioned to emit light or to receive light, and
- wherein the light-emitting diode and the photodiode each comprise, and share, an exposed sapphire substrate at which contact with living cells, together with the miniature differential interference contrast microscopy to realize the integrated sensing and imaging system.

2. The integrated sensing and imaging system according to claim 1, wherein the constructed miniature optical imaging module for differential interference contrast microscopy illuminates and receives linearly polarized light from the first prism that is split into two light rays, by the first prism, which two rays experienced different optical paths due to varied thicknesses of cell morphology, wherein the two light rays have different phases caused by the different optical paths, and wherein the constructed miniature optical imaging module for differential interference contrast microscopy generates amplitude fluctuations to form differential interference contrast microscopy images corresponding to the two light rays.

3. The integrated sensing and imaging system according to claim 1, wherein the first prism is disposed in a stacked position above the constructed miniature optical imaging module for differential interference contrast microscopy.

4. The integrated sensing and imaging system according to claim 1, wherein the monolithic optoelectronic chip comprises the light-emitting diode and the photodiode positioned to emit light or to receive light from the first prism.

5. The integrated sensing and imaging system according to claim 1,
- wherein light coupling from the light-emitting diode to the photodiode is achievable absent external optics due to the sharing of the sapphire substrate, and
- wherein the photodiode provides a photocurrent response, when living cells are in contact with the sapphire substrate, due to a refractive index difference between a first interface of the sapphire substrate and the living cells and a second interface of the sapphire substrate and a cell culture medium employed for the living cells.

* * * * *